(12) United States Patent
Alburty et al.

(10) Patent No.: US 8,110,112 B2
(45) Date of Patent: Feb. 7, 2012

(54) LIQUID TO LIQUID BIOLOGICAL PARTICLE CONCENTRATOR

(75) Inventors: David S. Alburty, Drexel, MO (US); Andrew E. Page, Kansas City, MO (US); Zachary A. Packingham, Drexel, MO (US); Daniel B. Marske, Lee's Summit, MO (US)

(73) Assignee: Innova Prep LLC, Drexel, MO (US)

( * ) Notice: Subject to any disclaimer, the term of this patent is extended or adjusted under 35 U.S.C. 154(b) by 610 days.

(21) Appl. No.: 12/131,015

(22) Filed: May 30, 2008

(65) Prior Publication Data

US 2009/0101575 A1 Apr. 23, 2009

Related U.S. Application Data

(60) Provisional application No. 60/932,271, filed on May 30, 2007, provisional application No. 60/961,391, filed on Jul. 20, 2007.

(51) Int. Cl.
*B01D 61/00* (2006.01)
*B01D 63/00* (2006.01)
*B01D 65/02* (2006.01)

(52) U.S. Cl. ............... 210/650; 210/636; 210/195.2; 210/639; 210/321.8; 134/12

(58) Field of Classification Search ............ 210/636, 210/650, 195.2, 639; 134/22.1, 22.12, 30
See application file for complete search history.

(56) References Cited

U.S. PATENT DOCUMENTS

| | | | |
|---|---|---|---|
| 4,381,775 A | 5/1983 | Nose' et al. | |
| 4,540,490 A | 9/1985 | Shibata et al. | |
| 4,574,052 A | 3/1986 | Gupte et al. | |
| 4,579,662 A * | 4/1986 | Jonsson | 210/636 |
| 4,680,025 A | 7/1987 | Kruger et al. | |
| 5,731,275 A * | 3/1998 | Prevost et al. | 510/161 |
| 5,883,143 A | 3/1999 | Eiben et al. | |

(Continued)

FOREIGN PATENT DOCUMENTS

EP 1248688 10/2002

(Continued)

OTHER PUBLICATIONS

PCT/US2008/06539 International Search Report and Written Opinion mailed Nov. 3, 2008, 9 pages.

(Continued)

*Primary Examiner* — Ana Fortuna
(74) *Attorney, Agent, or Firm* — Moazzam & Associates, LLC

(57) ABSTRACT

A rapid one-pass liquid filtration system efficiently concentrates biological particles that are suspended in liquid from a dilute feed suspension. A sample concentrate or retentate suspension is retained while eliminating the separated fluid in a separate flow stream. Suspended biological particles include such materials as proteins/toxins, viruses, DNA, and/or bacteria in the size range of approximately 0.001 micron to 20 microns diameter. Concentration of these particles is advantageous for detection of target particles in a dilute suspension, because concentrating them into a small volume makes them easier to detect. Additional concentration stages may be added in "cascade" fashion, in order to concentrate particles below the size cut of each preceding stage remaining in the separated fluid in a concentrated sample suspension. This process can also be used to create a "band-pass" concentration for concentration of a particular target size particle within a narrow range.

38 Claims, 20 Drawing Sheets

U.S. PATENT DOCUMENTS

| | | | |
|---|---|---|---|
| 5,902,476 A * | 5/1999 | Twardowski | 210/143 |
| 5,925,608 A * | 7/1999 | Spruyt et al. | 510/276 |
| 6,027,572 A | 2/2000 | Labib et al. | |
| 6,034,147 A | 3/2000 | Radovich et al. | |
| 6,086,856 A | 7/2000 | Saferstein et al. | |
| 6,147,133 A | 11/2000 | Sulzbach et al. | |
| 6,324,898 B1 | 12/2001 | Cote et al. | |
| 6,326,340 B1 | 12/2001 | Labib et al. | |
| 6,641,733 B2 | 11/2003 | Zha et al. | |
| 6,692,702 B1 | 2/2004 | Burshteyn et al. | |
| 6,692,968 B2 | 2/2004 | Burshteyn et al. | |
| 6,695,803 B1 | 2/2004 | Robinson et al. | |
| 6,817,984 B2 | 11/2004 | Robinson et al. | |
| 6,857,436 B2 * | 2/2005 | Labib et al. | 134/22.1 |
| 7,008,393 B2 | 3/2006 | Robinson et al. | |
| 7,141,171 B2 | 11/2006 | Lightfoot, Jr. | |
| 7,220,358 B2 * | 5/2007 | Schacht et al. | 210/636 |
| 7,354,773 B2 | 4/2008 | Rubio et al. | |
| 2002/0123154 A1 | 9/2002 | Burshteyn et al. | |
| 2002/0189647 A1 | 12/2002 | Labib et al. | |
| 2004/0132198 A1 | 7/2004 | Burshteyn et al. | |
| 2004/0132208 A1 | 7/2004 | Burshteyn et al. | |
| 2004/0229368 A1 | 11/2004 | Rubio et al. | |
| 2005/0098497 A1 | 5/2005 | Khudenko | |
| 2005/0184008 A1 * | 8/2005 | Schacht et al. | 210/636 |
| 2005/0244943 A1 | 11/2005 | Ladisch et al. | |
| 2007/0072287 A1 | 3/2007 | Morisette et al. | |
| 2007/0151924 A1 | 7/2007 | Mir et al. | |

FOREIGN PATENT DOCUMENTS

| | | |
|---|---|---|
| EP | 1633887 | 3/2006 |
| EP | 1707573 | 10/2006 |
| WO | WO03076089 A1 | 9/2003 |

OTHER PUBLICATIONS

Cummings, E.B. & Singh, A.K..; Dielectrophoretic Trapping Without Embedded Electrodes; Sandia National Laboratories; 2000; 10 pages.

BioPharm Enewsletter Case Study, "The Feasibility of Tangential Flow Filtration for Cell Lysate Clarification", Sep. 21, 2005, 5 pages.

LHC-110, Fluid Analytics, Inc., Product Overview, fluid-analytics. com, undated, 2 pages.

* cited by examiner

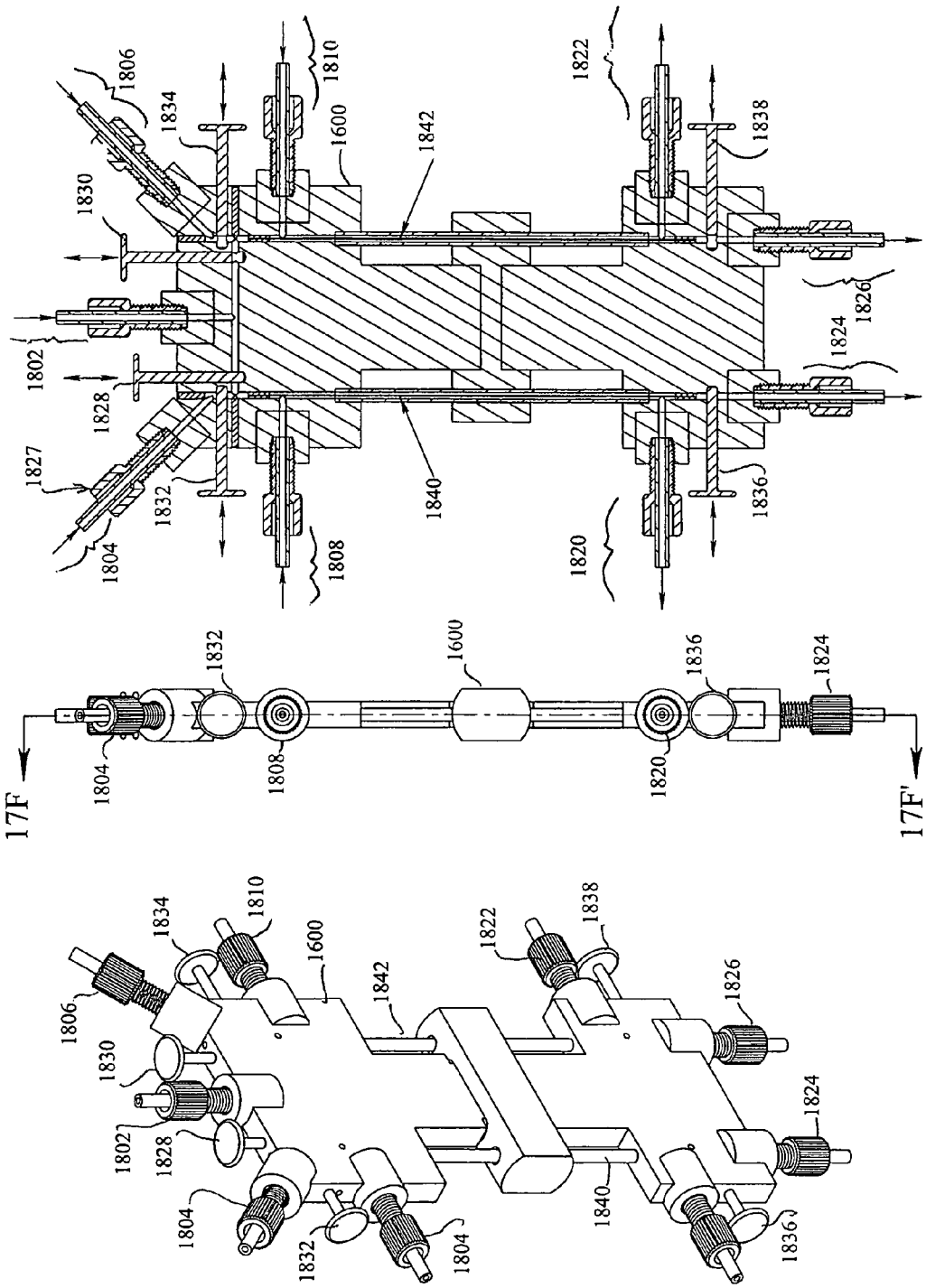

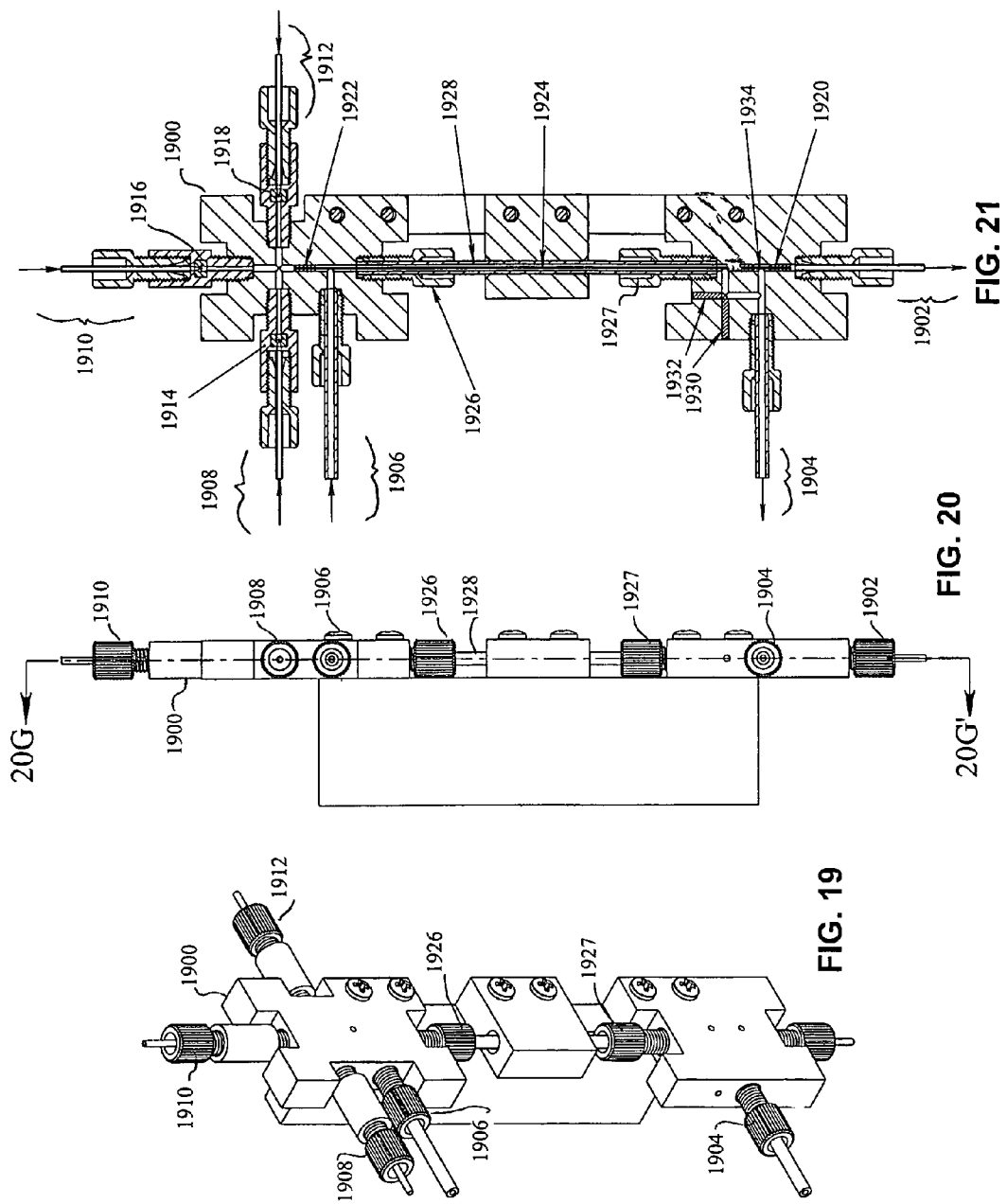

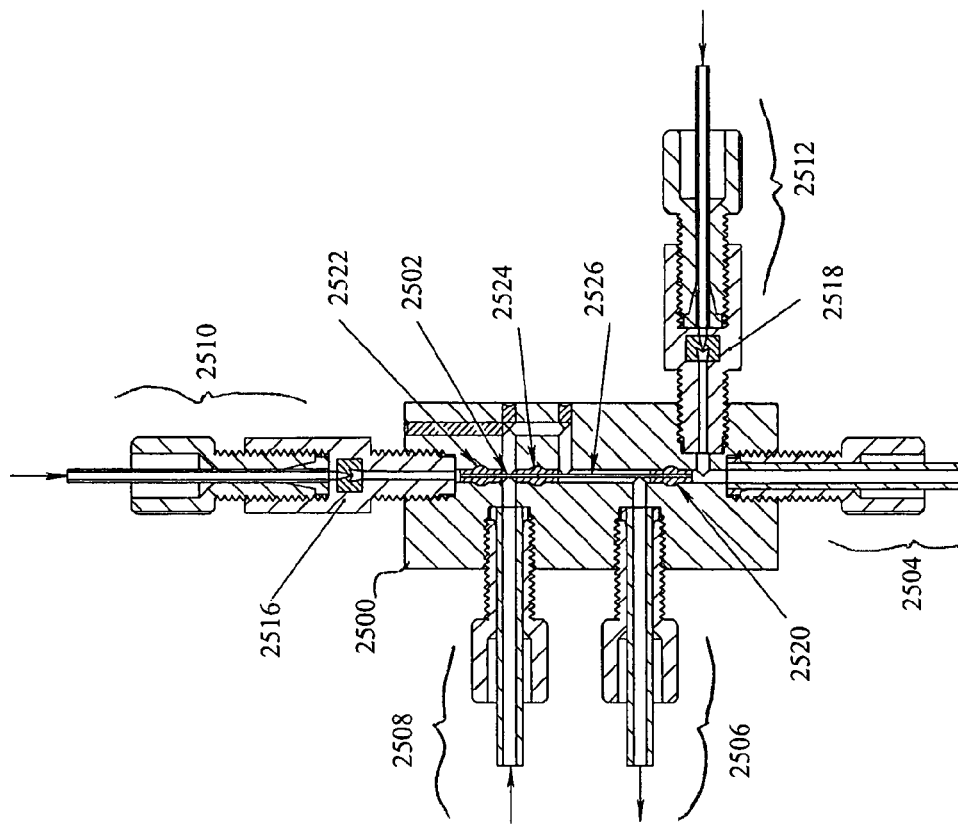
FIG. 27
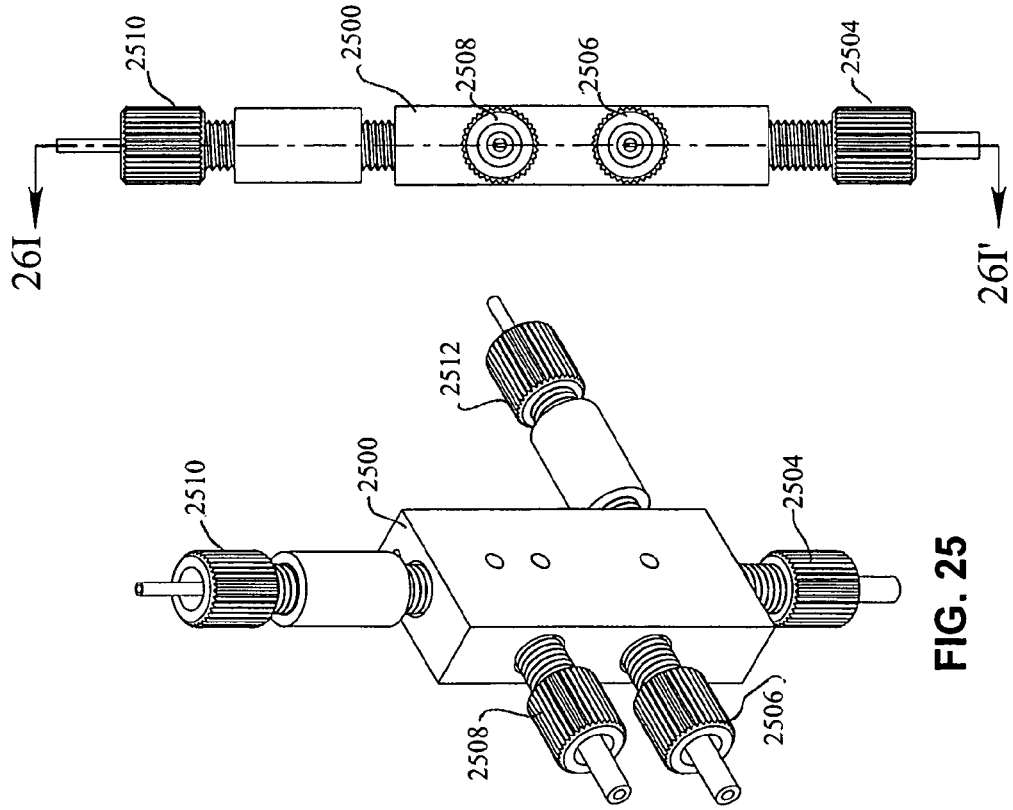
FIG. 26
FIG. 25

LIQUID TO LIQUID BIOLOGICAL PARTICLE CONCENTRATOR

RELATED APPLICATIONS

This application claims benefit of priority to U.S. Provisional Application Ser. Nos. 60/932,271 filed May 30, 2007 and 60/961,391 filed Jul. 20, 2007, both of which applications are hereby incorporated by reference to the same extent as though fully replicated herein.

BACKGROUND

1. Field of the Invention

The invention relates generally to the field of filtration systems. More particularly, the filtration system is used to concentrate dilute materials, such as biological particles, as may be useful in the arts of bioterrorism security, medicine, and environmental science.

2. Description of the Related Art

The difficulties of detecting and quantifying dilute materials in liquids are well known. Existing systems all begin to fail as concentration falls away until, eventually with diminished concentrations of analyte, there is an inability to detect at all. This poses a significant problem to national security where, for example, the postal anthrax attacks of 2001 and the subsequent war on terrorism have revealed shortcomings in the sampling and detection of biothreats. The medical arts are similarly affected by the existing limits on detection, as are the environmental sciences.

Just because existing systems have inherent detection limits does not mean that it is impossible to study analytes or particles for analysis that fall below these limits. It is possible to concentrate materials for analysis.

Particle concentration in liquid is traditionally performed using centrifugation. Centripetal force is used for the separation of mixtures according to differences in the density of components that form the mixture. This force separates a mixture forming a pellet of relatively dense material at the bottom of the tube. The remaining solution, which is alternatively called the supernate or supernatant liquid, may then be carefully decanted from the tube without disturbing the precipitate, or withdrawn with a Pasteur pipette. The rate of centrifugation is specified by the acceleration applied to the sample, and is typically measured in revolutions per minute (RPM) or g-forces. The particle settling velocity in centrifugation is a function of particle's size and shape, centrifugal acceleration, the volume fraction of solids present, the density difference between the particle and the liquid, and viscosity.

Problems with the centrifugation technique limit its applicability. The settling velocity of particles in the range of micron and smaller size particles is quite low and, consequently, centrifugal concentration of these particles takes several minutes to many hours. The actual time varies depending on the volume of the sample, the equipment used, and the skill of the operator. It is also difficult to segregate the particles into size ranges. Many successive centrifugations under carefully controlled circumstances may be used to separate particles into size fractions. In these separations, however, some portion of each sample will contain particles of all size fractions present. This is due to the presence of even the smallest particles in the mixture very near the bottom of the centrifugation vessel or tube at the start of the process.

Traditional flat filtration methodology is used to capture particles from a liquid onto a flat filter, which is usually supported on the back by a screen or fritted support. Many different methods of filtration exist, but all aim to attain the separation of two or more substances. This is achieved by some form of interaction between the substance or objects to be removed and the filter. The substance that is to pass through the filter must be a fluid, i.e. a liquid or gas. The simplest method of filtration is to pass a solution of a solid and fluid through a porous interface so that the solid is trapped, while the fluid passes through. This principle relies upon the size difference between the particles making up the fluid, and the particles making up the solid. In the laboratory, this if often done using a Büchner funnel with a filter paper that serves as the porous barrier.

One disadvantage of the physical barrier method of filtration is that the substance being filtered from the fluid will clog the channels through the filter over time. The resistance to flow through the filter becomes greater and greater over time as, for example, a vacuum cleaner bag. Accordingly, methods have been developed to prevent this from happening. Most such methods involve replacing the filter; however, if the filter is needed for a continuous process this need for replacement is highly problematic. Scraping and in-situ cleaning mechanisms may be used, but these can be unnecessarily complex and expensive.

In one example, bacteria may be removed from water by passing them through a filter supported in a Buchner funnel to trap the bacteria on the flat filter. Aerosol particles containing biological materials can also be trapped in the same way. For analysis, the trapped materials are often re-suspended in a known volume of liquid. This allows back-calculation of the original aerosol concentration. One method validated by the Edgewood Chemical Biological Center uses 47 mm glass-fiber filters to capture reference samples for biological analysis. The bacteria are extracted by soaking the filters overnight in 20 mL of buffered saline solution, then vortexed for 3 minutes to disrupt the filter material completely. Subsamples or aliquots of these suspensions are then provided for analysis by viable culture, PCR or other methods.

Tangential flow filtration is a variant of traditional filtration. This technique is sometimes called side-stream filtration or cross-flow filtration, and most often uses membrane systems to purify proteins. These systems circulate retentate across the membrane surface, which minimizes the fouling of the membrane. This arrangement provides longer membrane use, resulting in higher overall filtration efficiency. This process has been used in processing cell lysate to clean up the fluid for analysis of particular proteins. Millipore Corporation and Pall manufacture tangential flow filter cassettes that may be purchased on commercial order. Tangential flow systems are also used commercially for particles larger than proteins, and on scales larger than in the micron range.

The membrane in a tangential flow system may be a hollow fiber filter. These filters are commercially produced by a few companies, most notably Spectrum Laboratories, Inc. Hollow fiber filters may be constructed and arranged in packages intended for respective use in such intended environments of use as laboratories, small scale pharmaceutical production companies, and larger scale water treatment facilities.

Fluid Analytics, Inc. of Portland, Oreg. has developed a liquid sample concentrator that utilizes tangential flow across a flat filter and a proprietary controlled sonication method to efficiently remove collected particles. The unit has a flow rate of 20 ml/min with a sample volume of up to 20 ml and a concentrated volume of less than about 1 ml. The concentration efficiency is 90%.

Other technologies for concentration of biological particulate matter exist. Sandia National Laboratories, Massachusetts Institute of Technology and, other organizations have developed microfluidic devices that separate and concentrate particles by dielectrophoresis or electrophoresis. These units use microchannels and electric fields to move or collect particles. Sandia has also developed a system that concentrates particles at the interface between two immiscible liquids. Immunomagnetic particles are commercially available for use in the separation and concentration of bacteria.

Various methods exist for concentrating organisms in liquids prior to detection. Historically, the most common method is to enrich the sample in nutrient broth and then cultivate an aliquot of the broth on an agar plate. The biggest disadvantage of this method is the time requirement. It normally takes 5 to 7 days before organisms can be enumerated on the plates. Other concentration methods include various filtration based methods, adsorption-elution, immunocapture, flocculation, and centrifugation. It is problematic that to date no automated methods have been developed that can rapidly concentrate a large volume of water into a very small sample volume and do this task efficiently. In fact most of these methods fail in each of these areas, most notably efficiency of concentration, and ease of use.

A considerable amount of research has been performed using hollow fiber ultrafiltration to concentrate bacteria, viruses, and protozoa from large volumes of water. These methods all use variations of tangential flow or dead end filtration with concentration into water or a water and surfactant solution. Most of the methods described are not automated. Generally these systems are capable of concentrating 10 to 100 L water into 100 to 500 mL of concentrated sample; however, it is further problematic that none of the demonstrated technologies provides concentration into volumes of less than 100 mL. Even this volume is much larger than desired for the best possible detection when the concentrator systems are coupled with downstream detection apparatus. This means that a costly and time-consuming second manual concentration step is required to bring the final sample to the desired volume.

In bioterrorism defense detection systems an aerosol collector captures particles in the air and concentrates them into a liquid volume in the range of 1.5 ml to 15 ml. A portion of this sample is then transferred directly to a detector which analyzes the liquid and determines if any dangerous aerosols have been collected. Advanced, rapid microbiological detectors used in these systems are only capable of analyzing volumes from around 40 μL to 200 μL of liquid at a time. This volume is about 2% or less of a 10 mL sample from the collector. Any remaining fluid is either archived or dumped to waste.

SUMMARY

The present disclosure addresses the problem outlined above and advances the art by providing a highly efficient filtration system that can be quickly cleaned for resuspension of concentrated particles for analysis.

In one aspect, the disclosure herein teaches a method and device for concentrating biological particles that are entrained in a fluid. The concentrator cell or unit may use a single or plural hollow fiber filters, or other membranes in tangential flow devices. The filter may be extracted using a small volume of biologically and analytically compatible foamed wash buffer following the completion of the filtration cycle, in order to extract trapped particles from the filter.

Foam is as especially preferred medium for use in extracting the trapped particles because it has a relatively greater viscosity o or gel strength than regular liquid, and because is occupies a large volume that diminishes to a small amount of liquid when the foam collapses. The liquid portion of the foamed extraction wash material may be any liquid but is normally water with a buffer and surfactant added. The liquid may be held under pressure of, for example, 50 psi to 800 psi, with a water soluble gas such as carbon dioxide or nitrous oxide. One way to make a fine foam that is a minority of a percentage liquid by volume is to release the pressure and agitate the liquid through a mixing fret. The liquid fizzes to make the foam as the gas is released from solution under the reduced pressure. The foam flows through fluidic pathways extending from a permeate side of the filter, across the filter to a permeate side of the filter. In making this transit, the foam flow down the bore of the past the retentate side of the membrane (or down the bore of the hollow fiber) and out, thus extracting the captured particles. Because the gas in the foam escapes rapidly at atmospheric pressure, it quickly returns to a liquid so that it can be processed further as a liquid almost immediately after being dispensed.

The liquid extraction wash that is to be foamed may be formulated with a variety of additives. Any conventional buffering system may be used to control pH. Salts may be added, as well as foaming agents, film formers, thinners, thickeners, polymers, surfactants, functionalized particles, microspheres, silica particles, tagging materials, proteins, detergents, and other chemical, fluids, or particles. In one aspect, it is possible to add particles or microspheres or other agents that bind with analytes of interest, mix them with an incoming sample feed, and concentrate this sample feed for delivery to analytical equipment.

The foam may used to extract any number of enclosed surfaces that are added to the system feed for purposes of capturing particles, bacteria, viruses, protozoa, DNA, RNA, proteins, toxins, immunomagnetic beads, molecular probes, or other particles or molecules. The surfaces can include hollow fiber membranes; flat membranes; microsieves, including polymeric or silicon microsieves; silica surfaces (used to capture DNA in the presence of chaotropic salts such as guanidinium thiocyanate or sodium perchlorate); immunomagnetic beads; or other binding surfaces The use of hydrophobic membranes for sampling air (as the fluid, as opposed to aqueous samples); then extracting the membrane with the extraction foam.

Concentrator cells may be deployed in series; where the membrane surface area decreases with each cell. In this way, a very large sample can be processed by passing liquid through a cell with a very large surface area, then extracting with a large amount of foam (so the extraction is efficient), then passing the resultant fluid through a second cell that has much lower surface area than the first cell, that cell is then extracted with a much small amount of foam. So, the final sample volume is very small.

Vibrational energy, such as megasonic energy, ultrasonic energy, or other vibrations may be applied to the filter while passing the sample therethrough or during extraction of the membrane. This energy improves the fluid throughput rate and the extraction efficiency of the membrane surface.

It is possible to measure foam in a metered volumetric quantity, but also it is difficult to do. Use of a valve that is controlled with a timer may dispense reproducible volumes of foam by controlling the foam pressure and the valve opening time. Alternatively, a volumetric sample loop may be used, in combination with a multi-position valve, such as a rotary valve, for loading with highly reproducible volumes of foam.

It can be difficult to push gas across a hollow fiber filter membrane, especially when liquid has reached that membrane. Accordingly, in one aspect the system disclosed herein may selectively apply gas pressure to push foam through the system, especially across the filter. Gas pressure may provide needed energy to break up clogs in the retentate or at other locations in the system. Pressurized gas to store the hollow fiber, membrane, microsieves and/or the entire fluid path under high pressure gas, to act as a biocide, to reduce or stop biofilm build up or growth of organisms on the fiber, membrane, microsieves, or inside the system.

Two or more concentration cells with membranes of different pore sizes may be deployed in parallel, so that size fractionation can be performed. The use of foam for extraction lets much larger surfaces areas be used, which is very important for reducing blinding of the membranes and for allow highly efficient passage of particles smaller than the membrane pore size.

Since air does not readily travel through hydrophilic membranes of small pore size, various methods of getting aqueous samples to the hydrophilic membrane surface are disclosed. One technique includes pulling a vacuum on the retentate side of the membrane then allowing the fluid to move into the fiber retentate side. Since the hollow fibers may collapse under excessive pressures, it is also possible to pull a vacuum on the retentate side and permeate side of the membrane at the same time. It is also possible to provide a reservoir that is connected to the retentate side of the membrane, so when fluid is pushed into the fiber under pressure the air is compressed into this reservoir and the fluid moves to the membrane surface. Another option is to connect a hydrophobic membrane to the retentate side of the filter so that air will pass through the hydrophobic membrane until the aqueous fluid reaches the membrane.

Foam may be used for similar applications, such as extracting particles or molecules from other surfaces, then pulling the resultant liquid off of the surface with a squeegee and vacuum wand. That sample can then be concentrated with the concentrator.

Since the concentrator cell may be enclosed, it is capable of holding particles, bacteria, viruses, protozoa, DNA, RNA, proteins, toxins, immunomagnetic beads, molecular probes, microspheres or other particles or molecules in place on the membrane surface without extracting these particle with foam. The carrier fluid is removed then sample can be washed, tagged, or treated in other ways by pulling various wash buffers, EDTA, ethanol, lysis buffers, denaturing buffers, tagging solutions, immunomagnetic beads, immunobeads, silica beads, nanomaterials, or other liquids or particles.

In one aspect, these advantages may be obtained by using specially constructed concentrator cells that employ hollow fiber filters to concentrate samples for analysis. A foam extraction of trapped particles is particularly advantageous. The cell bodies are constructed with various ports that are operated in a specific sequence of events to trap particles of interest and then extract them using a foam extraction technique to provide a concentrated sample for analysis.

In one aspect, a novel one pass tangential flow filtration system offers significant advantages over previous methods of biological particulate matter concentration. This system concentrates the collected sample prior to analysis. The liquid volume of the sample is quickly reduced. As compared to centrifugation, which typically takes from 0 to 30 minutes to concentrate micron-sized particles, this process can be accomplished in 5 to 60 seconds for a 10 mL initial volume.

Unlike typical single-pass flat filtration, the sample remains in liquid form for transport and analysis. The detection limit for the target agent is lowered, with respect to the media originally sampled. The final sample volume is advantageously reduced much further than in previously known methods, while kept in liquid form, allowing detection in devices such as multi-well plate readers that utilize small input samples. The reduced-size samples can be more efficiently stored and transported by microfluidic handling methods. The device may be constructed to separate particles in one pass into different size fractions for analysis for certain agents. For example, cells and spores may be concentrated separately from viruses and biological toxins. Further, the size range that is concentrated can be narrow, or "band-pass" to concentrate a small size range fraction from a complex matrix, such as an environmental sample. The device may be used to reduce the onboard fluid storage capacity of aerosol samplers, by recycling the cleaned liquid back to the collection cycle after the sampled particles are removed into a small volume for analysis.

The instrumentalities disclosed herein are more readily adapted to automated systems than other technologies including centrifugation, flat filtration, and other methods. The flow-through nature of the device allows for straightforward configuration into an automated detection system.

The disclosed instrumentalities may be used in conjunction with biological collection/sampling systems where the resulting sample is contained in a liquid. Alternatively, the device could be coupled with a detection device that receives liquid samples. For many of these sampling and detection systems, it is advantageous to concentrate the sample prior to analysis, for reasons that are described below. In the field of medicine, in particular pathology, samples taken from patients may have a low concentration of an organism, virus, or toxin that causes illness, which must be identified in order to effect treatment. Concentration of such medical samples prior to analysis is also advantageous, for reasons that are described below. In the field of environmental science, field samples taken in the course of biological studies or investigations may contain biological materials of interest in low concentrations. Concentration of such materials is advantageous, for reasons that are described below. Additionally, for the three fields of interest described here, the device can be of further use in that by using a staged arrangement, concentrated samples may be separated by size if desired, without sacrificing concentration ability or efficiency. For the bioterrorism security field, a further advantage is the reduction in consumables (sampling fluid) that can be afforded by recycling the filtered penneate. Further, this concentration system is compatible with test particles, such as the Biological Particulate Matter Analogue, U.S. Pat. No. 7,179,596 (Page, Alburty, Brown, Huebner, 2007), a DNA-tagged polystyrene microsphere packaged in a metered dose aerosol dispenser and marketed by Sceptor Industries, Inc., as the "BioSim" for safely testing biological aerosol collection/detection systems.

The foregoing instrumentalities have significant utility in medical, environmental, or security applications. For example, concentration in the manner described facilitates aerosol sampling for pathogens or bioterrorism threat agents that can withstand being placed in a liquid sample for analysis. A list of such pathogens may be provided, for example, as recognized by the Centers for Disease Control. These organisms may be studied using conventional techniques that are facilitated by the concentration of samples as described above:

List 1: CDC Category A and B Bioterrorism Agents List
Category A (Definition Below)
Anthrax (*Bacillus anthracis*)
Botulism (*Clostridium botulinum* toxin)
Plague (*Yersinia pestis*)
Smallpox (*variola major*)

Tularemia (*Francisella tularensis*)
Viral hemorrhagic fevers (filoviruses [e.g., *Ebola, Marburg*] and arenaviruses [e.g., *Lassa, Machupo*])
Category B (Definition Below)
Brucellosis (*Brucella* species)
Epsilon toxin of *Clostridium perfringens*
Food safety threats (e.g., *Salmonella* species, *Escherichia coli* O157.H7, *Shigella*)
Glanders (*Burkholderia mallei*)
Melioidosis (*Burkholderia pseudomallei*)
Psittacosis (*Chlamydia psittaci*)
Q fever (*Coxiella burnetii*)
Ricin toxin from *Ricinus communis* (castor beans)
Staphylococcal enterotoxin B
Typhus fever (*Rickettsia prowazekii*)
Viral encephalitis (alphaviruses [e.g., Venezuelan equine encephalitis, eastern equine encephalitis, western equine encephalitis])
Water safety threats (e.g., *Vibrio cholerae, Cryptosporidium parvum*)
List 2: Secondary Potential Biological Threat Agents
  Viri/Prions
  Flaviviruses (Yellow fever virus, West Nile virus, Dengue, Japanese Encephalitis, TBE, etc.)
  Hep A, B, C
  Prions (CJD, BSE, CWD)
  Alphaviruses (VEE, EEE, WEE)
  Nipah virus
  Rabies virus
  Rhinovirus (could be modified?)
  Polioviruses
  Hantaviruses
  Filoviruses (*Ebola, Marburg, Lassa*)
  Bacilli
  *Mycobacterium tuberculosis*, drug resistant
  Mycobacteria other than TB, like *C. leprae*
  *Streptococcus pneumoniae*
  *S. pyogenes*
  *S. aureus*
  *Clostridium tetani*
  *C. difficile*
  *Bacillus cereus*
  *Coxiella brunette* (Q fever)
  *Francisella tularensis*
  *Borrelia recurrentis*
  *Rickettsia rickettsii*
  *R. prowazekii*
  *Shigella sonnei*
  *Bartonella henselae*
  *Yersinia enterolitica*
  *Y. pseudotuberculosis*
  *Neisseria meningitidis*
  *Legionella pneumophila*
  *Burkfholderia pseudomallei*
  *Pasturella multocida*
Other Pathogenic Microorganisms
  *Cryptosporidium parvum*
  *Histoplasma capsulatum*
  *Cryptococcus neoformans*
  *Aspergillus niger*
Pathogenic Fungi
  *Acremomium* spp.
  *Alternaria* alternate
  *Apophysomyces elegans*
  *Aspergillus terreus*
  *Bipolaris* spp.
  *Bipolaris spicifera*
  *Blastoschizomyces capitatus*
  *Candida krusei*
  *Candida lusitaniae*
  *Cladophialophora bantiana*
  *Cunnihamella berholletiae*
  *Curvularia lunata*
  *Exserohilum rostratum*
  *Fusarium moniliforme*
  *Fusarium solani*
  *Hansenula anomala*
  *Lasiodilodia theobromae*
  *Malassezia furfur*
  *Paecilomyces lilacinus*
  *Paecilomyces bariotii*
  *Penicillium marneffei*
  *Phialemonium curvatum*
  *Philophora parasitica*
  *P. richardsiae*
  *Ramichloridium* spp.
  *Rhizomucor pusillus*
  *Rhizopus rhizopodiformus*
  *Rhodotorula rubra*
  *Sacchromyces cerevisiae*
  *Scedosporium prolificans*
  *Trichosporon beigelii* (*T. asahii*)
  *Wangiella dermatitidis*
Physical Sizes of Some Agents and Surrogates:
Target:

| | |
|---|---|
| *Bacillus thuringiensis* endospore - | approximately 1 μm |
| *Bacillus anthracis* endospore - | approximately 1 μm |
| *Yersinia pestis* - | Gram negative rod-ovoid 0.5-0.8 μm in width and 1-3 μm in length |
| *Yersinia rohdei* - | approximately 1 μm |
| Venezuelan Equine Encephalitis - | 70 nm (0.07 μm) |
| Gamma-killed MS2 - | 2 mD or about 25 nm (0.025 μm) (but will pass through a 300 kD pore size but is retained by a 100 kD pore size Wick and McCubbin - ECBC) |
| Ovalbumin - | 45 kD or 6 nm (0.006 μm) |
| *Botulinum* Toxoid A - | 150 to 900 kD or 10 nm to 70 nm (0.01 μm to 0.07 μm)(Normally published as 150 kD how ever some publications state that toxoid A can be released as complexes comprised of the 150 kD toxin protein along with associated non-toxin proteins and can therefore be released in 900 kD, 500 kD, and 300 kD forms. |
| DNA - | 1000 Bp or 600 kD up to 15,000 Bp or 9 mD |

In other aspects, after concentration, detection of the threat agent(s) may be performed on nucleic acids that have been isolated as described above and amplified by conventional polymerase chain reaction (PCR) or PCR-like methods.

Detection or study of the agent(s) of interest may be performed by conventional immunoassay methods, or by ultraviolet light fluorescence methods.

Even if a threat agent is present, it is potentially useful to know that concentration and analysis resulting in a non-detect result can provide assurance that if the target agent is present, it is present in such a low quantity that the resulting risk to the affected population is minimal.

Separation of the sample into desirable size fractions may advantageously concentrate the target particles into separate but equally concentrated size fractions for analysis by different detection methods listed above, such as in separating and concentrating particles larger than 0.2 microns to segregate generally bacteria from other pathogens. A small size range or "band-pass" may be separated out and concentrated for interrogation for a particular threat agent or surrogate, such as by separating and concentrating particles from 0.2 microns diameter to 2 microns diameter to segregate most bacterial spores and concentrate them separately from smaller and larger particles present in the initial sample. It is also possible to separate and concentrate particles from 0.005 microns to 0.2 microns in diameter to separate most viruses and concentrate them separately from smaller and larger particles present in the initial sample. Actual test examples include viral equine encephalitis, or VEE; 0.06 microns in diameter.

Another mode of concentration may to separate and concentrate particles from 0.001 microns (approximately 5 kiloDaltons) to 0.01 microns (approximately 100 kiloDaltons) to separate toxins and proteins and concentrate them separately from smaller and larger particles present in the initial sample In other aspects, the above types of sampling and analysis are advantageously performed for the fields of homeland security, corporate security, and military force protection are useful when preceding work by automated sampling and analysis systems, such as those developed for government programs Portal Shield, Joint Programs Biological Detection System (JPBDS), US Postal Service Biological Detection System (BDS), and systems under development, such as the Biological Aerosol Networked Detection (BAND) system and Rapid Aerosol Biological Identification System (RABIS)

In other aspects, it is possible to test samples resulting from manual swabbing of surfaces onto wetted swabs, pads, or pieces of filter material, are often taken for bioterrorism security monitoring and typically extracted into a volume of liquid resulting in a 2 to 20 mL volume initial sample. Samples like these may be quickly concentrated to much smaller volumes in the range of 4-400 uL.

In still other aspects, samples my be concentrated for water sampling in search of bioterrorism agents, or in the interest of public health and safety, especially where a sample may contain target agent(s) that are thought to be a threat to the health of humans, animals or plants, causing societal disruption and economic harm. Agricultural products and livestock environments may also be studied by the instrumentalities herein disclosed.

Additional fields of use include medical research and diagnostics. For example, sample concentration is useful in cancer research where very low concentrations of experimental drugs in body fluids or urine are the targets of analysis, and in allergy diagnosis where low quantities of specific antigens are the targets of analysis in body fluids. Health effects research may also benefit by determining health effects known to be caused by various materials in inhaled particulate matter with aerodynamic diameter below 2.5 microns (PM 2.5). Benefit is seen in the field of forensic medicine where low concentrations of toxins or venoms are the targets of analysis in body fluids. Other aspects of use may include the study of operating rooms for surface extraction and air monitoring of pathogens, as well as pharmaceutical manufacturing where the biological aerosol particulate matter concentration is regulated by the United States Food and Drug Administration.

In other aspects, environmental studies may benefit to include any types of sampling and analysis that are performed for the field of environmental study, such as in assessing health effects through research regarding various materials in inhaled particulate matter with aerodynamic diameter below 2.5 microns (PM 2.5) or high altitude aerosol research where low quantities of particulate are collected and must be concentrated for study. These instrumentalities may benefit cleanrooms where very low aerosol concentrations of aerosol particles are collected for monitoring that is aimed at source control.

Commercially available hollow fiber filter tubes are arranged in the device such that the dilute feed suspension is fed under pressure in a single pass into one end of the tubes, while excess cleaned water is removed under vacuum from a space surrounding the tubes. The working pressure is the differential pressure between the feed pressure and the cleaned liquid side of the filters. This arrangement accelerates the process compared to the use of pressure only on the feed and recycling the retentate several times, as is done normally (for example, Millipore Corporation's Pellicon 3 System for concentrating monoclonal antibodies, Spectrum Laboratories KrosFlo Research II System). An air bleed valve on the retentate side is opened at the start of the filtration process to bleed out air from the inside of the filter. Bleeding this air is essential to fast initiation of the filtration cycle when using a hydrophilic filter as air will not pass through a hydrophilic membrane of small pore size. Balancing the pressure appropriately by providing gas pressure on the permeate side of the filter during the extraction process improves extraction efficiency.

To further improve the efficiency of the concentration device, a biocompatible surfactant such as Triton X-100 is added to the feed at low levels, such as 0.1-0.01% by volume. This liquid is an insignificant volumetric addition, but can increase the efficiency of concentration from the 40% to 65% range to nearly 100%. Buffered surfactant solutions such as 0.1% tris buffered saline (TBS) or phosphate buffered saline (PBS) with 0.01 to 0.1% Triton or Tween are commonly used in the collection fluids of bioaerosol samplers.

Mechanical shear such as produced by a shaker motor, or an ultrasonic or megasonic horn is also used to improve throughput efficiency and processing speed.

Hollow fiber filters made of different materials are used for application specific reasons. Such fibers are commonly made of mixed cellulose esters (ME), polyethersulfone (PES), polysulfone (PS), polypropylene (PP) polyacrylonitrile (PAN) and hydrophilic polydivinylidene fluoride (PVDF) and other materials such as stainless steel and ceramics. Various advantages and disadvantages accrue to each type of filter. Some design criteria are size of pores, biocompatibility, smoothness, fouling potential, and physical strength.

Cleaning and decontamination of hollow fiber filters is desirable when the device is used to concentrate multiple samples. Cleaning and decontamination of PES filters, such as the ones used in the devices of Embodiments 1 and 2 can be performed using 3% hydrogen peroxide or 0.5% sodium hypochlorite (10% dilution of commercially available bleach). PS and PES filters can also be autoclaved and steam-cleaned. Cleaning of these filters cannot be performed using ethyl acetate (typically used to dissolve polystyrene microspheres used for performance testing) or acetone, which dissolves PES. PES-compatible solvents include water, carbonated water, methanol, ethanol, hexane, and ether. Triton X-100 surfactant is compatible with the PES hollow fiber filters.

Sample extraction may be performed into a small volume using foam made from the extraction surfactant. This procedure cleans the concentrator, while simultaneously enhancing extraction efficiency and allowing for greatly reduced retentate volumes. A small volume of liquid may be used to create a large volume of foam. Since the boundaries of the bubbles present in the foam must remain intact to remain as foam, the boundaries of the bubbles at the interface of the filter and the extraction foam must always be touching. As the foam proceeds through the hollow fiber filter, it sweeps the concentrate through the device. When the foam is extracted from the device and collapses, the remaining product is a small volume of liquid. This volume will normally be in a range of less than 5 microliters to 1 milliliter, but may be up to 100 milliliter or more for use in extraction of large filter surface areas. In its simplest form, the foam may be made in a separate container, then injected to sweep the sample from the concentrator into the sample collection port. However, the use of a sample loop to measure the amount of liquid used to make the foam is preferred in order to generate samples of consistent size. In addition to surfactant foams that are generated by mixing air and a surfactant solution, foam may also be generated with a carbonated surfactant solution. Following carbonation, the solution is agitated by dispensing through an orifice, frit, filter, or capillary tube. The Triton foam extraction methods described here can also be used for extraction and cleaning of other collection surfaces in aerosol samplers and collectors. The use of foam to extract these surfaces can provide a significant increase in extraction efficiency and significant decrease in final sample volume.

BRIEF DESCRIPTION OF THE DRAWINGS

FIG. 1 shows a three dimensional perspective view of a concentrator cell according to a first embodiment;

FIG. 2 shows a right side elevational view of the concentrator cell shown in FIG. 1;

FIG. 3 shows a midsectional view of the concentrator cell taken along line 2A-2A' of FIG. 2;

FIG. 4 shows a three dimensional perspective view of a concentrator cell according to a second embodiment;

FIG. 5 shows a right side elevational view of the concentrator cell shown in FIG. 4;

FIG. 6 shows a midsectional view of the concentrator cell taken along line 5B-5B" of FIG. 5;

FIG. 7 shows a three dimensional perspective view of a concentrator cell according to a third embodiment;

FIG. 8 shows a right side elevational view of the concentrator cell shown in FIG. 7;

FIG. 9 shows a midsectional view of the concentrator cell taken along line 8C-8C' of FIG. 8;

FIG. 10 shows a three dimensional perspective view of a concentrator cell according to a fourth embodiment;

FIG. 11 shows a right side elevational view of the concentrator cell shown in FIG. 10;

FIG. 12 shows a midsectional view of the concentrator cell taken along line 11D-11D' of FIG. 11;

FIG. 13 shows a three dimensional perspective view of a concentrator cell according to a fifth embodiment;

FIG. 14 shows a right side elevational view of the concentrator cell shown in FIG. 13;

FIG. 15 shows a midsectional view of the concentrator cell taken along line 14E-14E' of FIG. 14;

FIG. 16 shows a three dimensional perspective view of a concentrator cell according to a sixth embodiment;

FIG. 17 shows a right side elevational view of the concentrator cell shown in FIG. 16;

FIG. 18 shows a midsectional view of the concentrator cell taken along line 17F-17F' of FIG. 17;

FIG. 19 shows a three dimensional perspective view of a concentrator cell according to a seventh embodiment;

FIG. 20 shows a right side elevational view of the concentrator cell shown in FIG. 19;

FIG. 21 shows a midsectional view of the concentrator cell taken along line 20G-20G' of FIG. 20;

FIG. 22 shows a three dimensional perspective view of a concentrator cell according to an eighth embodiment;

FIG. 23 shows a right side elevational view of the concentrator cell shown in FIG. 22;

FIG. 24 shows a midsectional view of the concentrator cell taken along line 23H-23H' of FIG. 23;

FIG. 25 shows a three dimensional perspective view of a concentrator cell according to a ninth embodiment;

FIG. 26 shows a right side elevational view of the concentrator cell shown in FIG. 25;

FIG. 27 shows a midsectional view of the concentrator cell taken along line 26I 26I' of FIG. 26;

FIG. 28 shows a three dimensional perspective view of a concentrator cell according to a tenth embodiment;

FIG. 29 shows a right side elevational view of the concentrator cell shown in FIG. 28;

FIG. 30 shows a midsectional view of the concentrator cell taken along line 29J-29J' of FIG. 29;

FIG. 31 shows a three dimensional perspective view of a concentrator cell according to an alternate embodiment with respect to that shown in FIG. 28;

FIG. 32 shows a right side elevational view of the concentrator cell shown in FIG. 31;

FIG. 33 shows a front elevational view of the concentrator cell shown in FIG. 31;

FIG. 34 shows a three dimensional perspective view of a concentrator cell according to an eleventh embodiment;

FIG. 35 shows a right side elevational view of the concentrator cell shown in FIG. 34;

FIG. 36 shows a midsectional view of the concentrator cell taken along line 35K-35K' of FIG. 35;

FIG. 37 shows a three dimensional perspective view of a concentrator cell according to a twelfth embodiment;

FIG. 38 shows a right side elevational view of the concentrator cell shown in FIG. 37;

FIG. 39 shows a midsectional view of the concentrator cell taken along line 37L-37L' of FIG. 38;

FIG. 40 shows an automated concentration system, which is depicted in a schematic layout wherein any of the foregoing concentrator cells may be used;

FIG. 41 shows an automated concentration system, which is depicted in a schematic layout wherein any of the foregoing concentrator cells may be used;

FIG. 41A provides expanded detail with respect to a feature of FIG. 41;

FIG. 42 shows an extraction foam generator according to a first embodiment, as depicted in a three dimensional perspective view;

FIG. 43 shows a right side elevational view of the extraction foam generator shown in FIG. 42;

FIG. 44 shows a midsectional view of the extraction foam generator taken along line 43N-43N' of FIG. 43;

FIG. 45 shows an extraction foam generator according to a second embodiment, as depicted in a three dimensional perspective view in combination with the concentrator cell shown in FIG. 13;

FIG. 46 shows a right side elevational view of the extraction foam generator shown in FIG. 45;

FIG. 46A provides additional detail with respect to a feature of FIG. 45;

DETAILED DESCRIPTION

There will now be shown and described one or more concentrator cells that are provided with a tangential flow media which may be used to concentrate biological particles and subsequently extracted with foam to obtain, for example, concentrated proteins, microorganisms, and/or nucleic acids.

Figure 3:
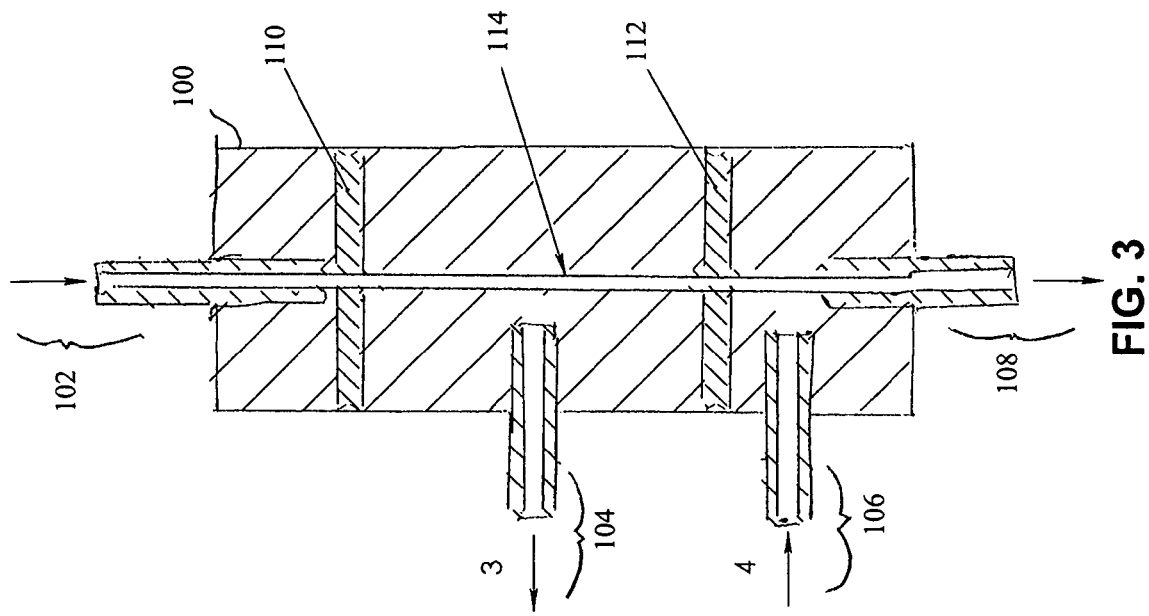
Figure 2:
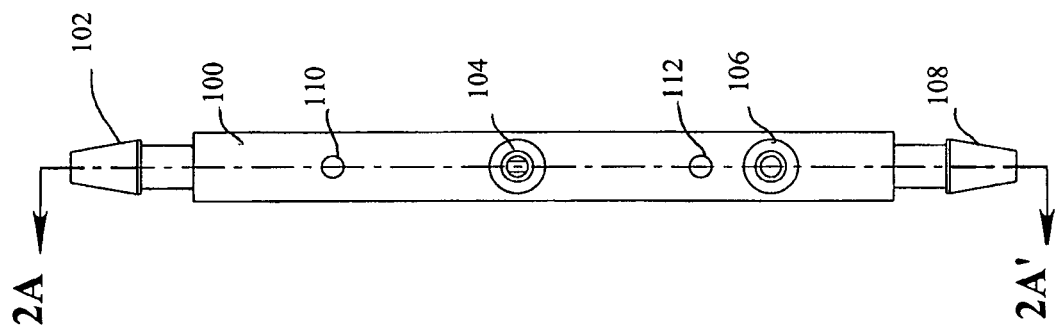
Figure 1:
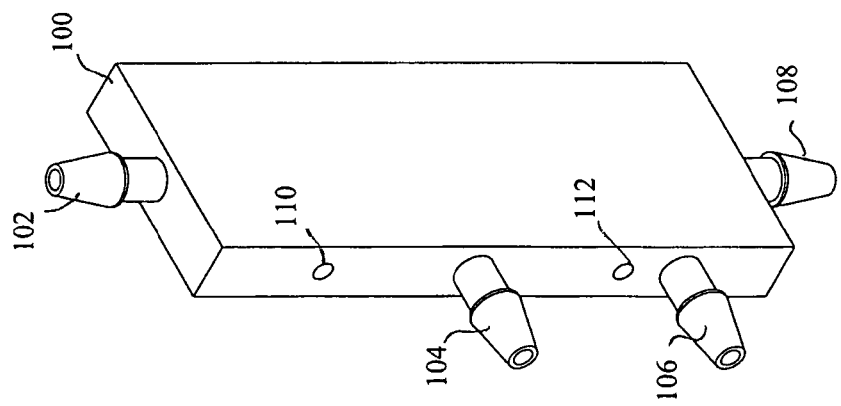

FIGS. 1, 2 and 3 shows a concentrator cell 100 that may be constructed from a rectangular block of plastic or metal that is drilled to create various fluid channels. Barbed fittings are glued in place for tubing connections to form ports 102, 104, 106, 108. Flexible tubing (not depicted) may be attached to the ports 102-108, and pinch clamps or valves (also not depicted) may be used to control flow through this tubing. These structures function as valves or flow control mechanism which are understood to be present in proximity to each fluidic port in this disclosure for operation according to the functionality described therewith, whether or not the flow control device is actually depicted A potting material, such as glue 110, 112, holds a hollow fiber filter 114 in place. As used herein, the term "potting material" means a destructible or removable material that is used to anchor a hollow fiber filter, and which may be removed for renewal of the filter. FIG. 3 shows the internal fluid channels together with respective arrows indicating the direction of fluid flow in each of ports 102, 104, 106, 108. The respective ports include an extraction fluid flush port 102, permeate port 104, feed port 106, and retentate port 108.

Concentrator cell 100 operates as follows. The retentate port 108 and extraction fluid flush port 102 are closed at the start of the sample concentration process. A vacuum is optionally applied at the permeate port 104, and the feed is introduced under pressure at the feed port 106. The sample then passes through the hollow fiber filter 114. When the entire feed sample has passed through the hollow fiber filter the pressure and vacuum are equalized between ports 104, 106, then the feed port 106 is closed. A vacuum is applied to the retentate port 108 and the flush port 102 is opened allowing a small, pre-measured volume of surfactant liquid or foam to flush the captured particles off of the inside surface of the hollow fiber filter, producing the desired final volume of concentrated fluid.

Figure 6:
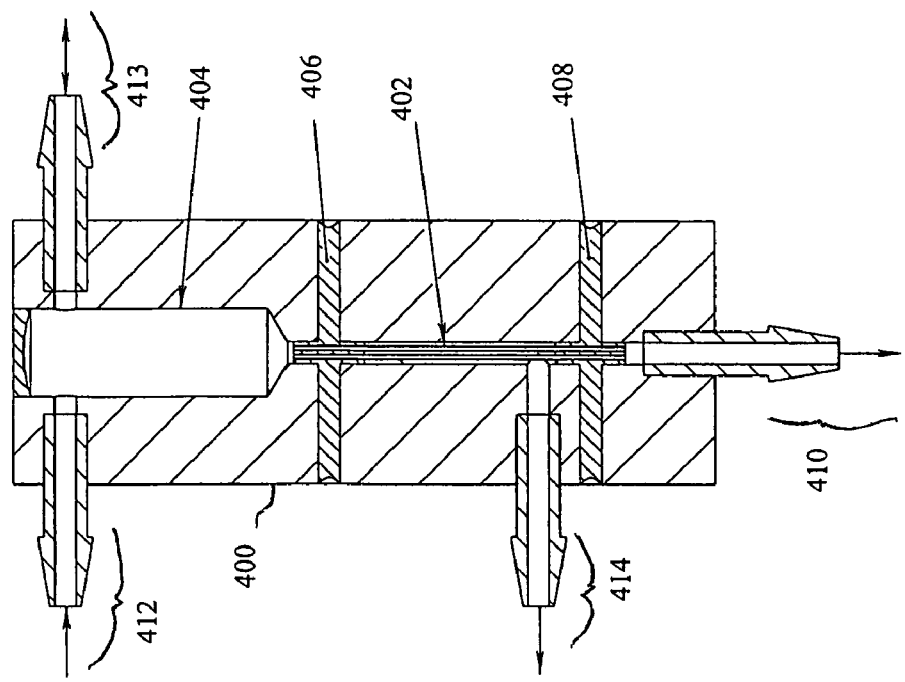
Figure 5:
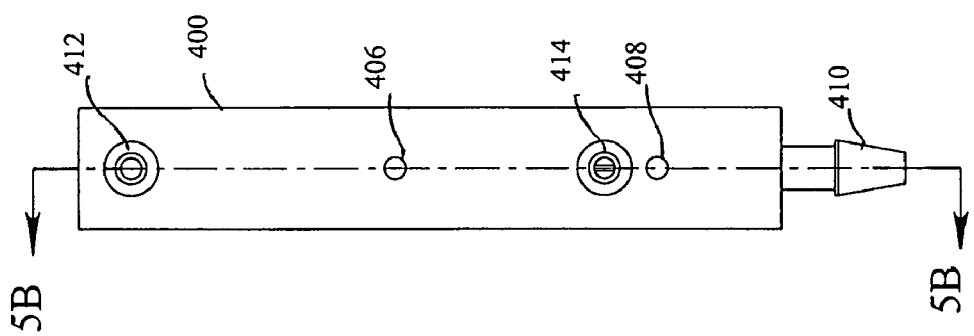
Figure 4:
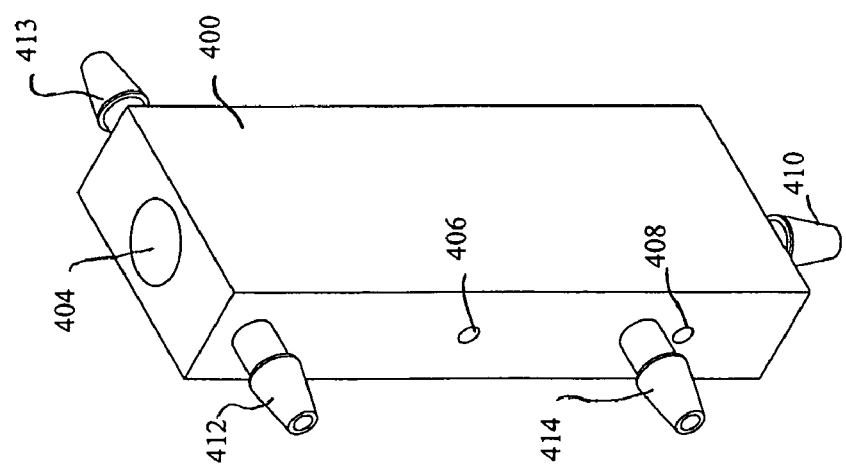

FIGS. 4, 5 and 6 show a concentrator cell 400. Cell 400 resembles cell 100; however, two hollow fiber filters 402 are used instead of one, and an integrated reservoir 404 retains a predetermined volume of the feed sample which is used to flush the fibers 402 at the end of the concentration cycle. Potting material 406, 408 retains the hollow fiber filters 402 in place. FIG. 6 shows the internal fluidic pathways together with arrows indicating flow direction at each of the retentate port 410, feed port 412, is the purge port 413, and permeate port 414.

Concentrator cell 400 operates as follows. The retentate port 410 is closed and the purge port 413 is opened. Feed is injected under pressure through the feed port 412 until the reservoir 404 is full, then the purge port 413 is closed. A vacuum is applied to the permeate port 414 and pressure is applied to the feed port 412. Once the feed sample has been completely injected, the pressures are equalized at ports 412, 414, then the feed port 412 is closed and the retentate port 410 is opened with vacuum there being applied. The purge port 413 is opened and the feed remaining in the reservoir 404 is used to flush the captured particles off of the inside surface of the hollow fiber filters 402, producing the desired final volume of concentrated fluid.

Figure 9:
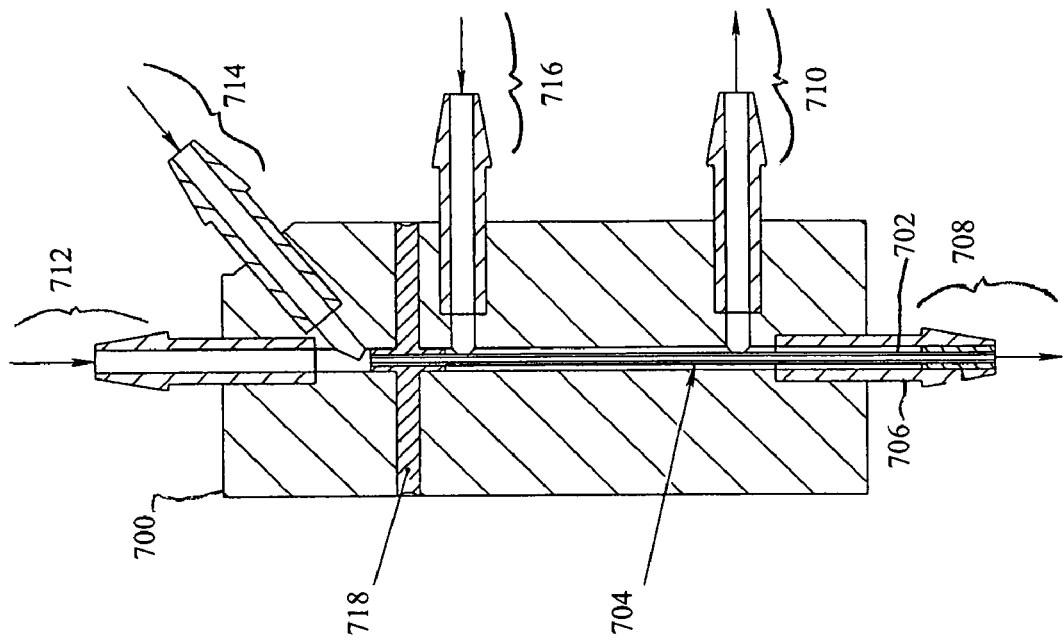
Figure 8:
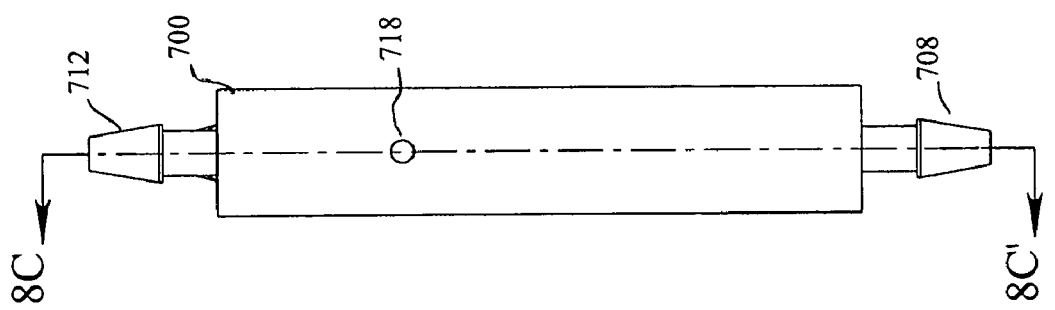
Figure 7:
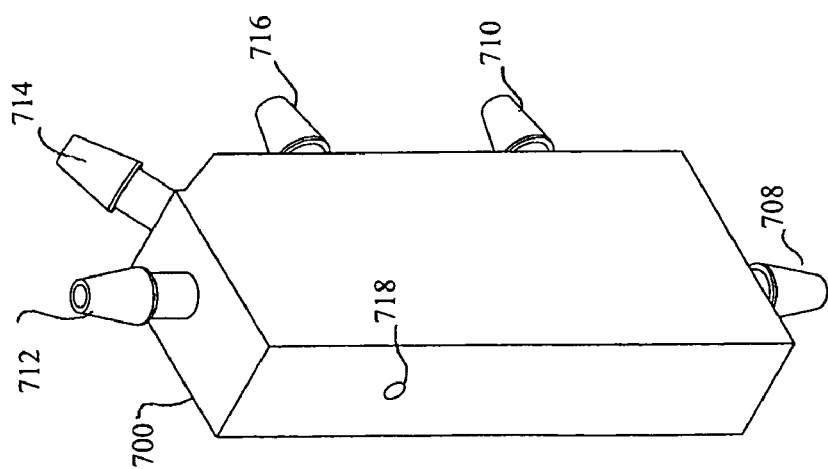

FIGS. 7, 8 and 9 show a third embodiment indicated as concentrator cell 700. Concentrator cell 700 is similar to that of concentrator cell 100. As shown in FIG. 9, distal portion 702 of a hollow fiber filter 704 is potted in a barbed insert 706 mounted in a retentate port 708. This arrangement advantageously minimizes dead volume in the retentate port 708 for improved sample concentration. A permeate purge port 710 is added to facilitate the removal of the permeate fluid that is trapped around the outside of the fiber at the end of the feed cycle. FIG. 9 shows internal pathways of fluidic communication through the concentrator cell 700 with arrows indicating flow direction at each of the retentate port 708, feed port 712, permeate port 710, extraction fluid port 714, and permeate purge port 716. Potting material 718 retains the hollow fiber filter 704 in place.

Concentrator cell 700 operates as follows. The retentate port 708 is opened and the feed is injected through the feed port 712 to purge air from inside the hollow fiber filter 704. The retentate port 708 is then closed and pressure is applied to the feed port 712 as a vacuum is applied to the permeate port 710. Once the feed has all been injected, the feed pressure is equalized across ports 708, 710, and the permeate purge port 716 is opened. Thus, remaining permeate fluid is pulled through the permeate port 710 while the permeate pressure is equalized. The retentate port 708 is next opened and a pre-measured volume of extraction fluid is injected under pressure through the extraction fluid port 714 to flush the captured particles off of the inside surface of the hollow fiber filter 704, producing the desired final volume of concentrated fluid.

Figure 12:
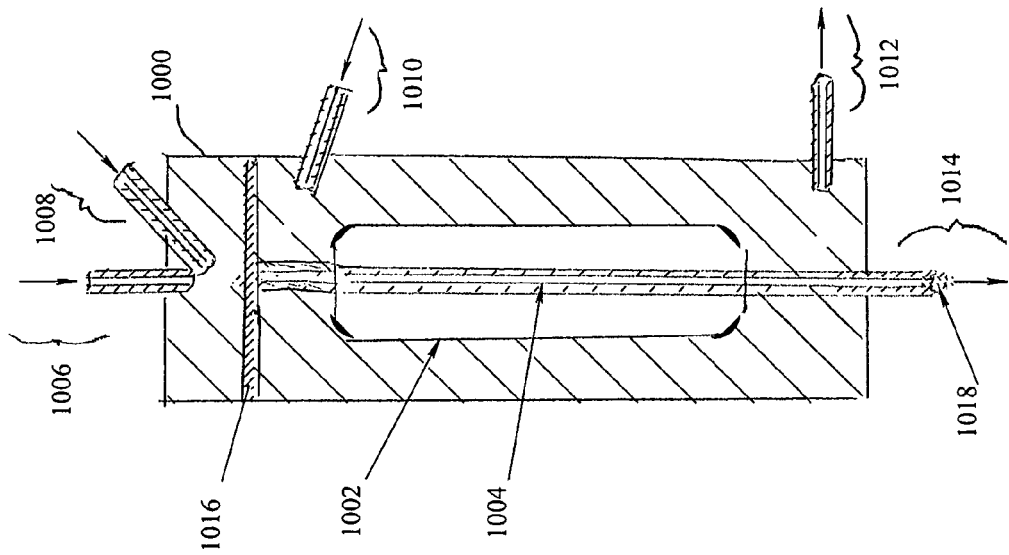
Figure 11:
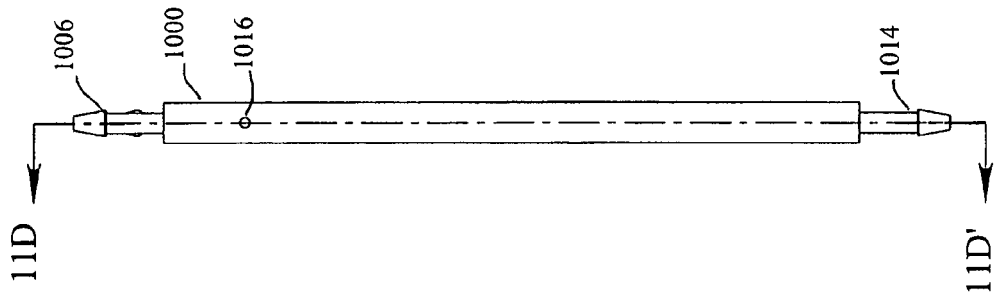
Figure 10:
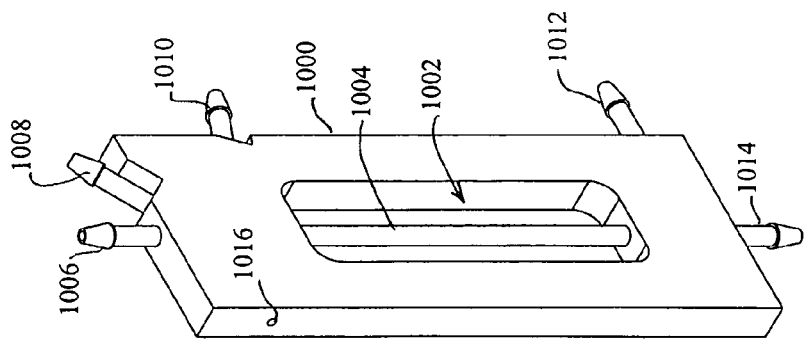

FIGS. 10, 11 and 12 show yet another embodiment indicated as concentrator cell 1000. Concentrator cell 1000 is similar to that of concentrator cell 700, but has a central opening 1002 fitted with a flexible tube 1004 that may be removed to facilitate easier replacement of a hollow fiber filter 1006. FIG. 12 shows the internal flow pathways within concentrator cell 1000 together with arrows indicating flow direction at each of feed port 1006, extraction fluid port 1008, permeate purge port 1010, permeate port 1012, and retentate port 1014. Potting materials 1016, 1018 retain the hollow fiber filter 1004.

Operation of concentrator cell 1000 proceeds as in the case of concentrator cell 700. The retentate port 1014 is opened and a feed is injected through the feed port 1006 to purge air from inside the hollow fiber filter 1004. The retentate port 1014 is then closed and pressure is applied to the feed as a vacuum is applied to the permeate port 1012. Once the feed has all been injected, the feed pressure is equalized across ports 1006, 1014. The permeate purge port 1010 is opened and remaining permeate fluid is pulled through the permeate port 1012 while the permeate pressure is equalized. Then, the retentate port 1014 is opened and a pre-measured volume of extraction fluid is injected under pressure through the extraction fluid port 1008 to flush the captured particles off of the inside surface of the hollow fiber filter 1004, producing the desired final volume of concentrated fluid.

Figure 15:
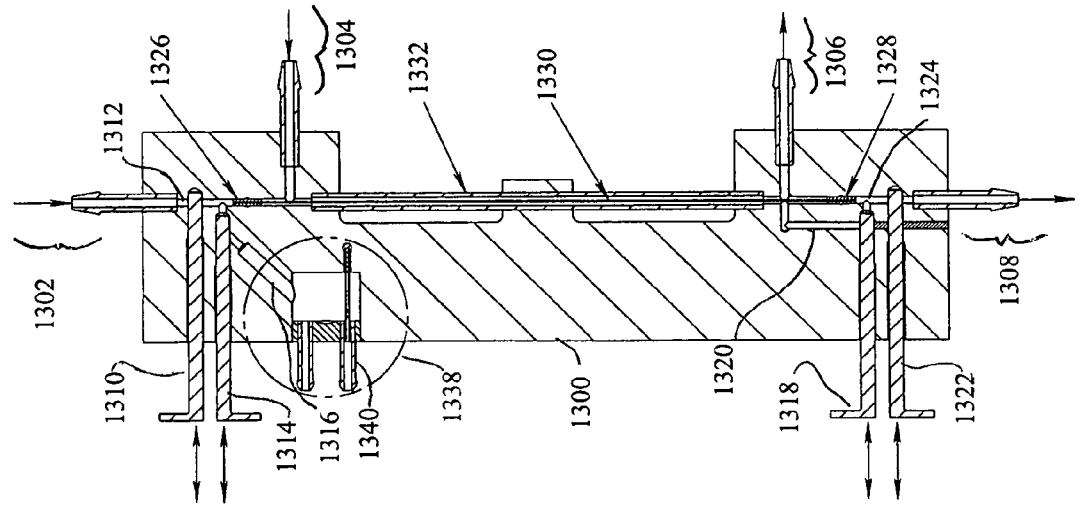
Figure 14:
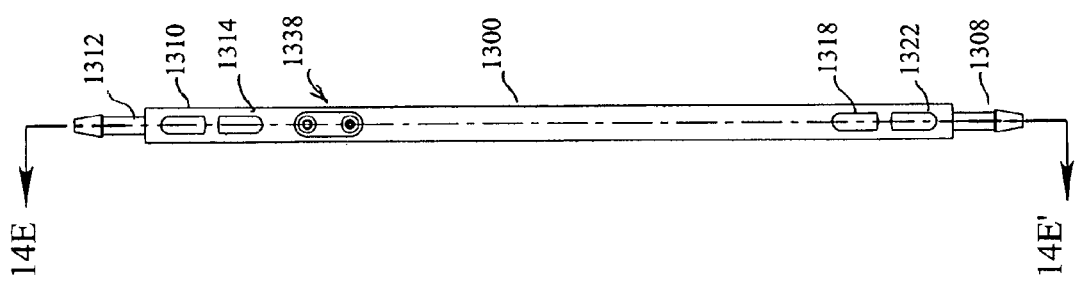
Figure 13:
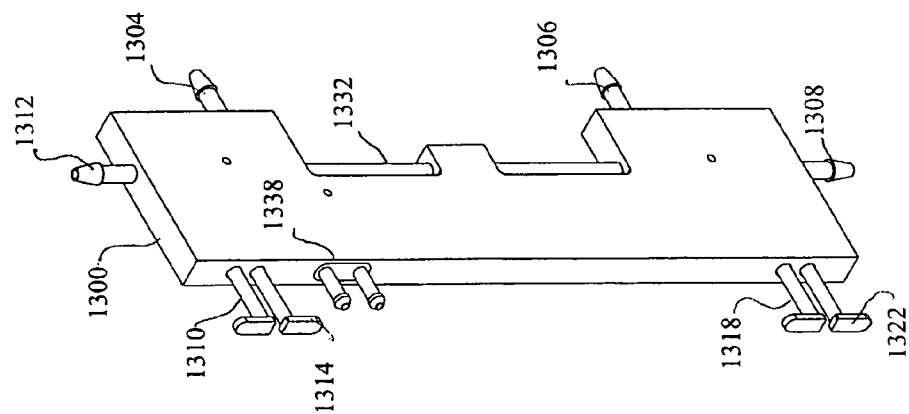

FIGS. 13, 14, and 15 show concentrator cell 1300, which has additional features with respect to previous embodiments. Concentrator cell 1300 includes integrated feed, extraction fluid, air bleed, and retentate valves, and an integrated foam extraction fluid generator. The potting holes are drilled in the plane perpendicular to the fluid channels to decrease their length and make the cell more compact. The removable center tube introduced in embodiment 4 is also used. This is the first cell which utilizes surfactant foam for the extraction fluid, which greatly increases extraction efficiency and decreases the final concentrated sample volume. FIG. 15 shows each component of concentrator cell 1300 with arrows indicating the direction of fluid flow in each port. The ports include feed port 1302, permeate purge port 1304, permeate port 1306, and retentate port 1308. An elongate shiftable feed valve 1310 controls flow through passageway 1312. An elongate shiftable extraction fluid valve 1314 controls flow through passageway 1316. An elongate shiftable air bleed valve 1318 controls passageway 1320, while an elongate shiftable retentate valve 1322 controls passageway 1324. Potting materials 1326, 1328 are advantageously disposed in parallel to the flow direction through hollow fiber filter 1330, thus decreasing the length of the potting materials and eliminating the necessity of drilling additional holes to receive the potting materials. A removable tube 1332 facilitates replacement of the hollow fiber filter 1330. Feature 1338 indicates an extraction foam generator 1340 that is described in additional detail below.

Concentrator cell 1300 operates as follows. The feed valve 1310 and the air bleed valve 1318 are opened, and the feed fluid is slowly fed into the feed port 1302. Air in the hollow fiber filter 1330 is forced out, and when the feed fluid reaches the bottom of the hollow fiber filter 1330 the air bleed valve 1318 is closed. Vacuum is then applied to the permeate port 1306, and the feed fluid is forced through the hollow fiber filter 1330. When the feed fluid has been pushed completely through, the permeate purge port 1304 is opened to flush the liquid around the outside of the hollow fiber filter 1330 out the permeate port 1304. The pressure on the hollow fiber filter is then equalized between the feed port 1302 and permeate port 1306, then the feed valve 1310 is closed. Then, the retentate valve 1322 and the extraction fluid valve 1314 are opened. The extraction foam generator 1340 is then used to flush the captured particles off of the inside surface of the hollow fiber filter 1330 until the desired final volume of concentrated fluid is reached.

FIGS. 16, 17, and 18 introduce the concept of a 'cascade' or 'band pass' system 1600 allowing for concentration and separation of different target particle size ranges. Also, high pressure liquid chromatography (HPLC) style compression fittings are used to make the port connections which are more durable and can withstand higher pressures than barbed connectors. FIG. 18 shows each component with arrows indicating the direction of fluid flow in each of extraction foam port 1802, feed A port 1804, feed B port 1806, permeate purge A port 1808, permeate purge B port 1810, is the permeate A port 1820, permeate B port 1822, retentate A port 1824, retentate B port 1826. Each of these ports is provided with a HPLC-style compression fitting, for example, as fitting 1827 (see FIG. 18). Elongate shiftable valves control flow through associated fluidic pathways including extraction foam A valve 1828, extraction foam B valve 1830, feed A valve 1832, feed B valve 1834, retentate A valve 1836, retentate B valve 1838. Filters include hollow fiber filter 1840 and hollow fiber filter 1842.

In this "band pass" configuration, hollow fiber filter A 1840 captures particles over a certain size, for example two micron, and passes smaller particles entrained with the remaining fluid into the permeate A port 1820. Feed B port 1806 is fluidically connected to permeate A port 1820. Hollow fiber filter B 1842 captures all of the particles that hollow fiber filter A 1840 passes into the permeate A port 1820. In this example, system 1600 operates according to the principles described above; however, everything below a predetermined size cutoff, such as particles of two microns or less or even particle-free fluid, passes through the permeate B port 1822.

FIGS. 19, 20 and 21 show a concentrator cell 1900 that is designed to facilitate starting a concentration cycle when the hollow fiber filter is wet and there is gas in the system. Hydrophilic fibers allow water based solutions to pass through them easily; however, gas can not pass through the wet fiber due to the capillary action of the water in the fiber pores. This essentially causes the fiber to lock up until the gas is purged from the inside of the fiber. This problem was addressed in previous embodiments by opening the retentate valve until the feed solution forced all of the gas out of the fiber; however, this is problematic for systems that are automated under a system of electronic controls. This embodiment introduces the use of a short hydrophobic fiber inline with the main hydrophilic fiber. The hydrophobic fiber allows gas to flow through it but not liquid, so the gas is effectively purged from the fiber automatically.

Another new feature of this embodiment is a gas injection port which allows any extraction foam left in the fiber to be forced out through the retentate port without adding to the final extracted liquid volume. Furthermore, from this design forward the concentration process includes pressurizing the permeate side of the hollow fiber filter with gas while the extraction foam is being injected. This prevents the extraction foam from pushing through the fiber and into the permeate.

FIG. 21 shows each component of concentrator cell 1900 where arrows indicate the direction of fluid flow in each of retentate port 1902, permeate port 1904, permeate purge port 1906, feed port 1908, extraction foam port 1910, and gas injection port 1912. Valves 1914, 1916, and 1918 are one-way check valves permitting flow in the directions indicated. Potting material 1920, 1922 retains a hollow fiber filter 1924. HPLC compression fittings 1926, 1927 allow quick removal and replacement of the hollow fiber filter 1924 mounted also within hollow tube 1928. Potting material 1930, 1932 seals channels connecting the hydrophobic and hydrophilic fiber permeate sides. A hydrophobic fiber is located downstream of hollow fiber filter 1924.

Concentrator cell 1900 operates as follows. The retentate valve 1902 is closed and a vacuum is applied to the permeate port 1904. This forces feed solution into the feed port 1908. Any gas trapped in the feed side of the hollow fiber filter 1924 is forced out through the hydrophobic fiber 1934. Once the feed solution has all passed through the hydrophilic fiber 1924, the permeate purge port 1906 is opened and the pressure is equalized across the surface of the fibers. Then, gas pressure is applied through the permeate port 1904, and the retentate port 1902 is opened. A predetermined volume of extraction foam is injected under pressure through the extraction foam port 1910 to flush the captured particles off of the inside surface of the hollow fiber filter 1924. Finally, gas is forced through the gas injection port 1912, which forces any remaining foam out of the hollow fiber filter 1924, producing the desired final volume of concentrated fluid.

Figure 24:
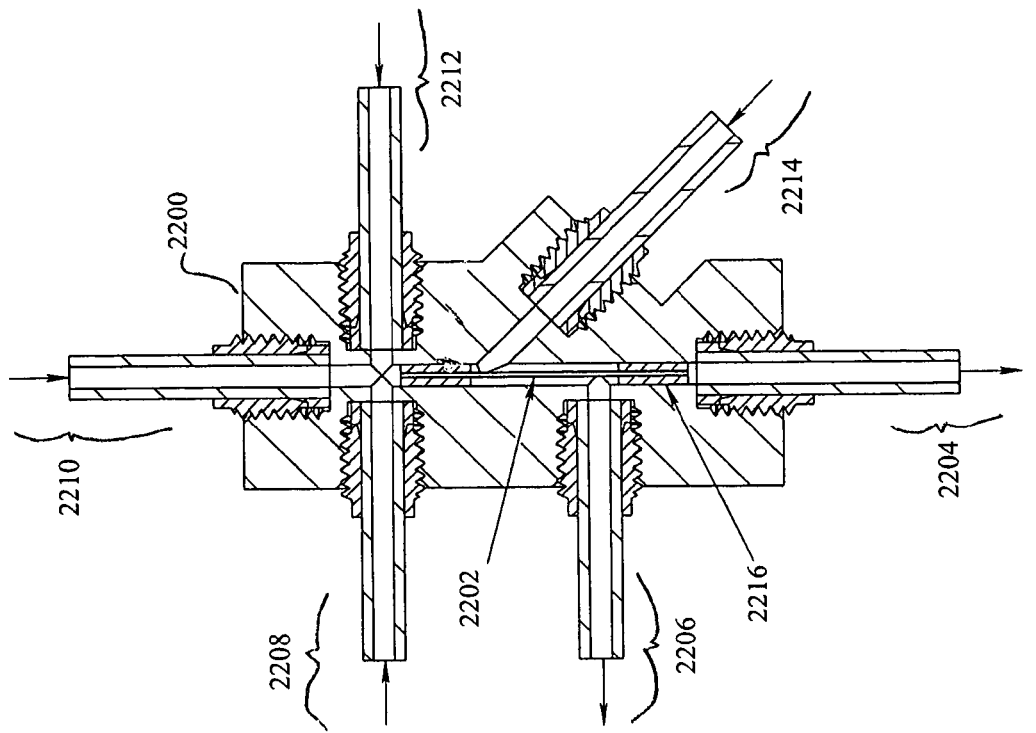
Figure 23:
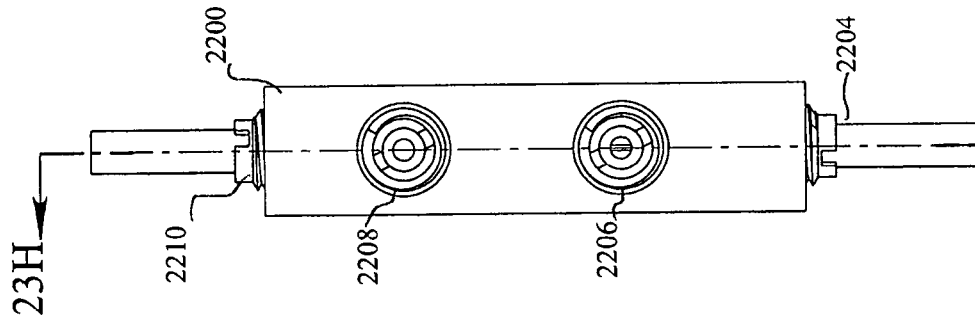
Figure 22:
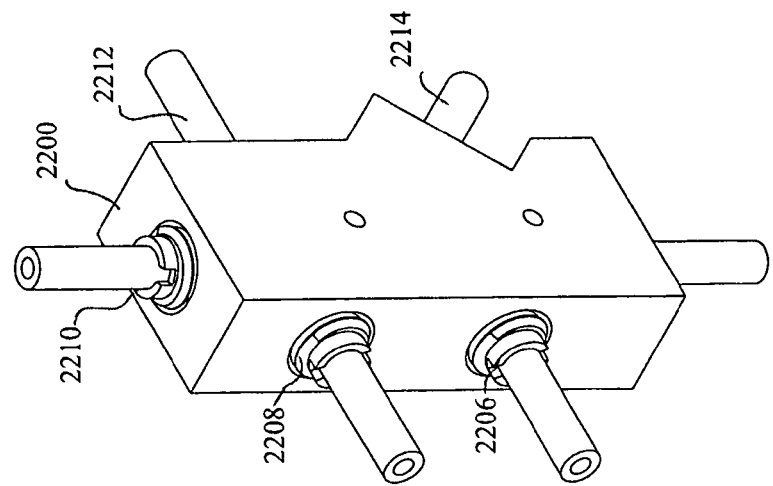

FIGS. 22, 23 and 24 show an embodiment identified as concentrator cell 2200, which is a compact design for use where size of the concentrator cell is an issue. Concentrator cell 2200 contains, for example, a hollow fiber filter 2202 that is less than one inch long. FIG. 24 shows each component of concentrator cell 2200 with arrows indicating the direction of fluid flow in each of retentate port 2204, permeate port 2206, feed port 2208, extraction foam port 2210, gas injection port 2212, and permeate purge port 2214. Potting material 2216 retains hollow fiber filter 2218.

Concentrator cell 2200 operates as follows. The retentate valve 2204 is opened and a vacuum is applied to the permeate port 2206. The feed solution is injected through the feed port 2208 until the feed solution reaches the end of the hollow fiber filter 2202. Then the retentate port 2204 is closed. When the feed solution has all been forced through the hollow fiber filter 2202, the permeate purge port 2214 is opened to remove the remaining fluid around the hollow fiber filter 2204 and equalize the pressure across the fiber surface. Gas pressure is next applied through the permeate port 2206. The retentate port 2204 is opened, and extraction foam is injected through the extraction foam port 2210 to flush the captured particles off of the inside surface of the hollow fiber filter 2202. Finally, gas is forced through the gas injection port 2212, which forces any remaining foam out of the hollow fiber filter 2202, producing the desired final volume of concentrated fluid.

FIGS. 25, 26 and 27 show an embodiment according to concentrator cell 2500 which, by way of example, combines the hydrophobic fiber section for gas removal from concentrator cell 1900 with the small size of concentrator cell 2200. The main changes from previous embodiments are the lack of a gas injection port, and the feed port has been relocated to the bottom of the cell. The feed port was moved to help ease the clearing of clogs in the fiber. Concentrator cell 2500 may also contain a hollow fiber filter 2502 that is less than one inch long. FIG. 27 shows each component of concentrator cell 2500 with arrows indicating the direction of fluid flow in each of retentate port 2504, permeate port 2506, permeate purge port 2508, extraction foam port 2510, and feed port 2512. Valves 2516, 2518 are one-way check valves. Numerals 2520, 2522, 2504 indicate potting material. A hydrophilic hollow fiber filter 2526 assists with the purging of internal gas under system automated control, as is described above.

Concentrator cell 2500 operates as follows. The retentate port 2504 is closed and a vacuum is applied to the permeate port 2506. Feed solution is forced into the feed port 2512. Any gas trapped in the feed side of the hollow fiber filter 2502 is forced out through the hydrophobic fiber 2526. Once the feed solution has all passed through the hydrophilic fiber 2526, the penneate purge port 2508 is opened and the pressure is equalized across the surface of the fibers. Then, gas pressure is applied through the permeate port 2506, and the retentate valve 2504 is opened. A predetermined volume of extraction foam is injected under pressure through the extraction foam port 2510 to flush the captured particles off of the inside surface of the hollow fiber filter, producing the desired final volume of concentrated fluid.

Figure 30:
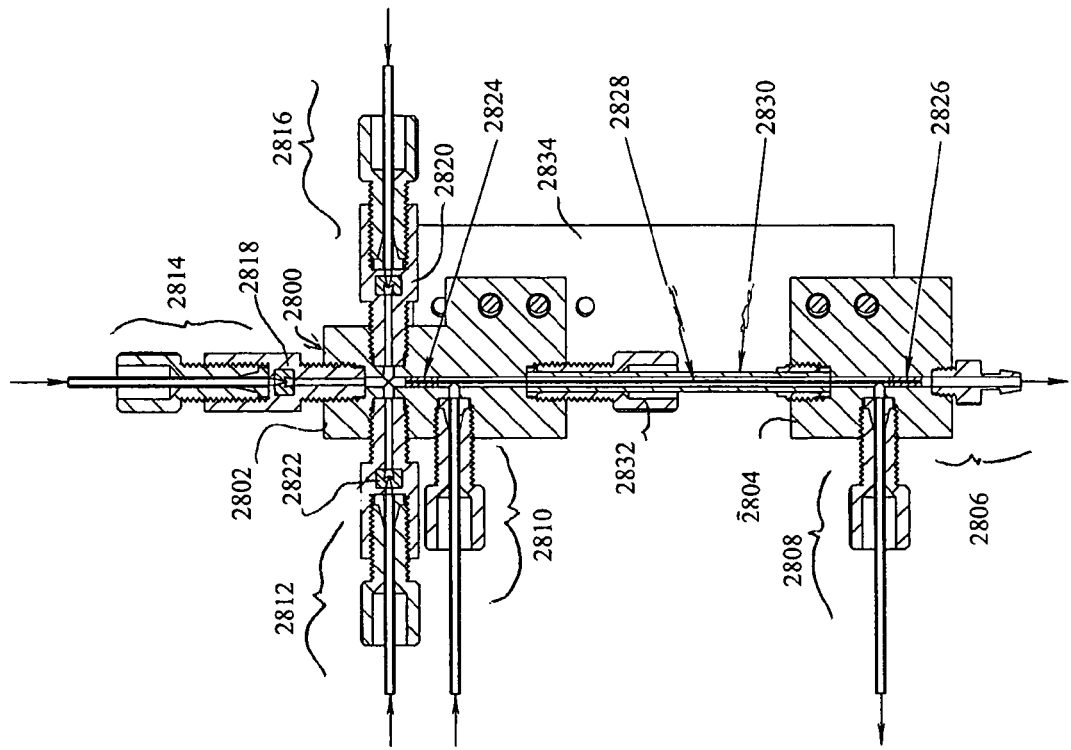
Figure 29:
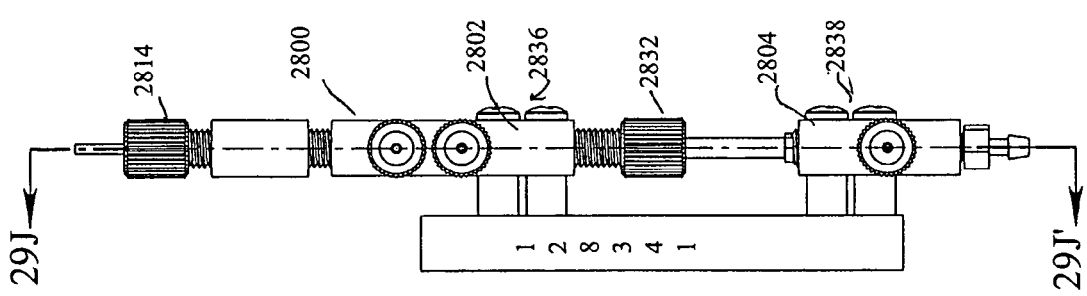
Figure 28:
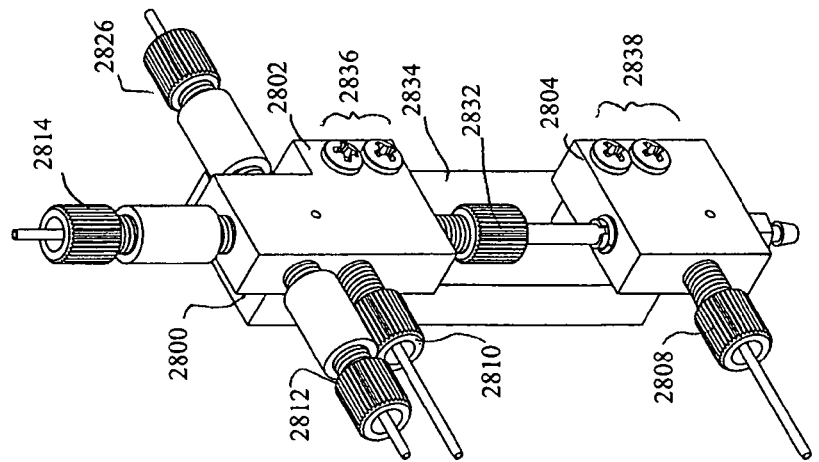

FIGS. 28, 29, and 30 show concentrator cell 2800 according to another embodiment. Concentrator cell 2800 is very similar to concentrator cell 2200 except, by way of example, concentrator cell 2800 is made up of modular components that allow different length fibers to be used in the same cell by changing the tube between the respective upper and lower manifolds 2802, 2804.

FIG. 30 shows each component of concentrator cell 2800 where arrows indicate the direction of fluid flow in each of retentate port 2806, permeate port 2808, purge port 2810, feed port 2812, extraction foam port 2814, and gas injection port 2816. Valves 2818, 2820, and 2822 are one-way check valves. Potting material 2824, 2826 retains hollow fiber filter 2828, as does a hollow tube 2830 and compression fitting. A modular bar 2834 may be provided in various lengths to adjust the assembly for selected lengths of hollow fiber filter 2828, and this modular bar may be secured with fasteners 2836, 2838.

Concentrator cell 2800 operates as follows. Retentate valve 2806 is opened and a vacuum is applied to the permeate port 2808. Feed solution is injected through the feed port 2812 until the feed solution reaches the end of the hollow fiber filter 2828. Then the retentate port 2806 is closed. When the feed solution has all been forced through the hollow fiber filter 2828, the permeate purge valve 2810 is opened to remove the remaining fluid around the hollow fiber filter 2828 and equalize the pressure across the fiber surface. Gas pressure is next applied through the permeate port 2808, and the retentate valve 2806 is opened. A predetermined volume of extraction foam is injected through the extraction foam port 2814 to flush the captured particles off of the inside surface of the hollow fiber filter 2828. Finally, gas is forced through the gas injection port 2820, which forces any remaining foam out of the fiber and produces the desired final volume of concentrated fluid.

Figure 33:
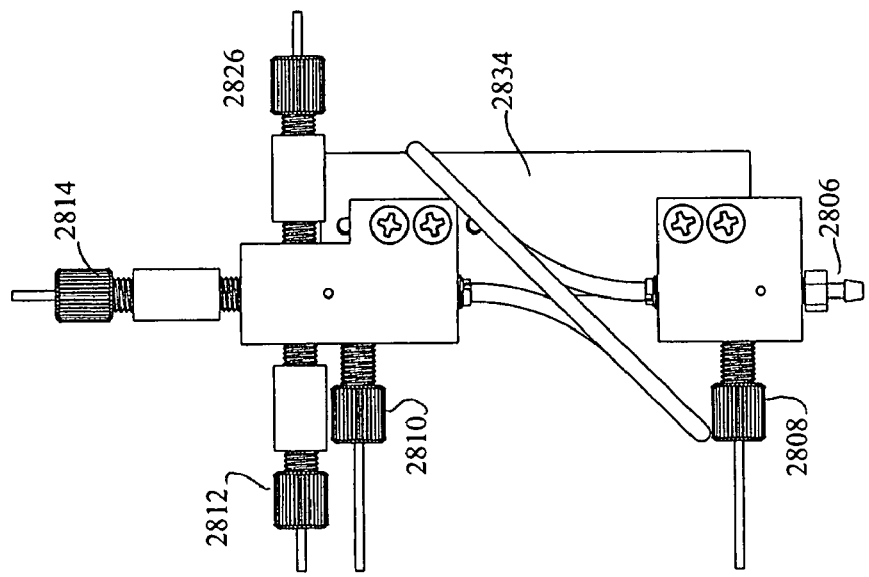
Figure 32:
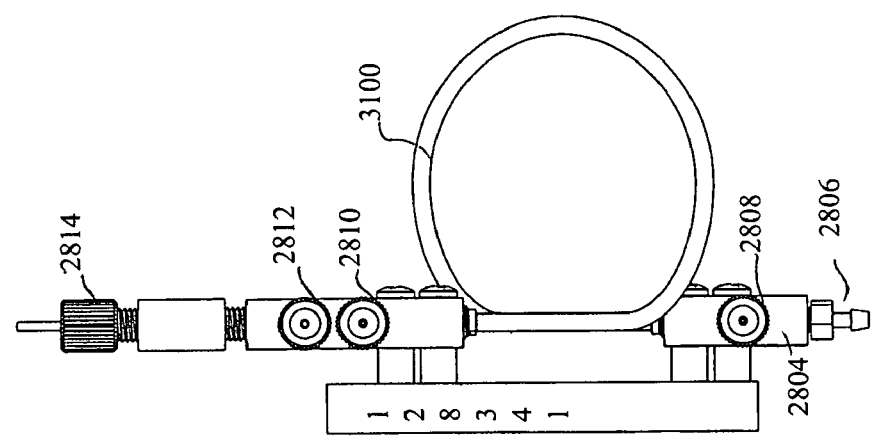
Figure 31:
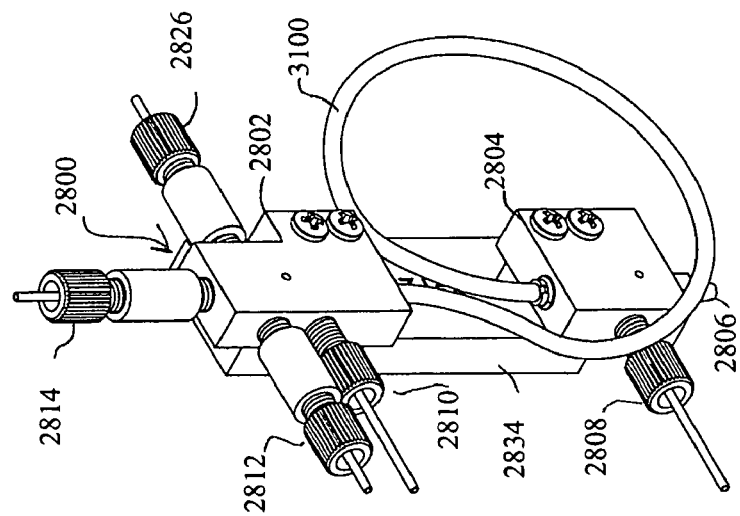

FIGS. 31, 32 and 33 show the concentrator cell 2800 in an alternate configuration where there is a looped fiber 3100. This configuration allows long fibers to be used without greatly increasing the size of the concentrator cell.

Figure 34:
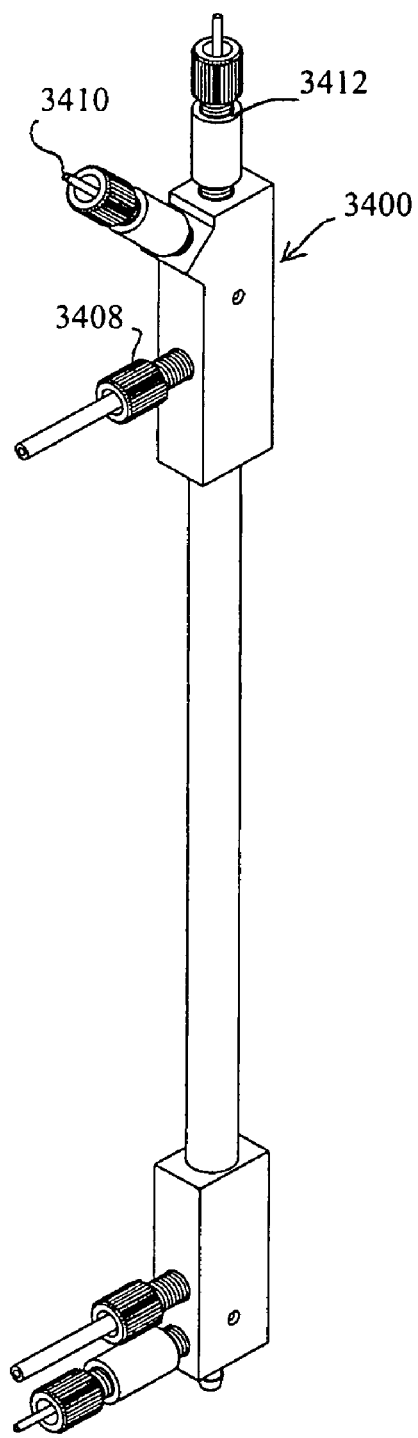
Figure 35:
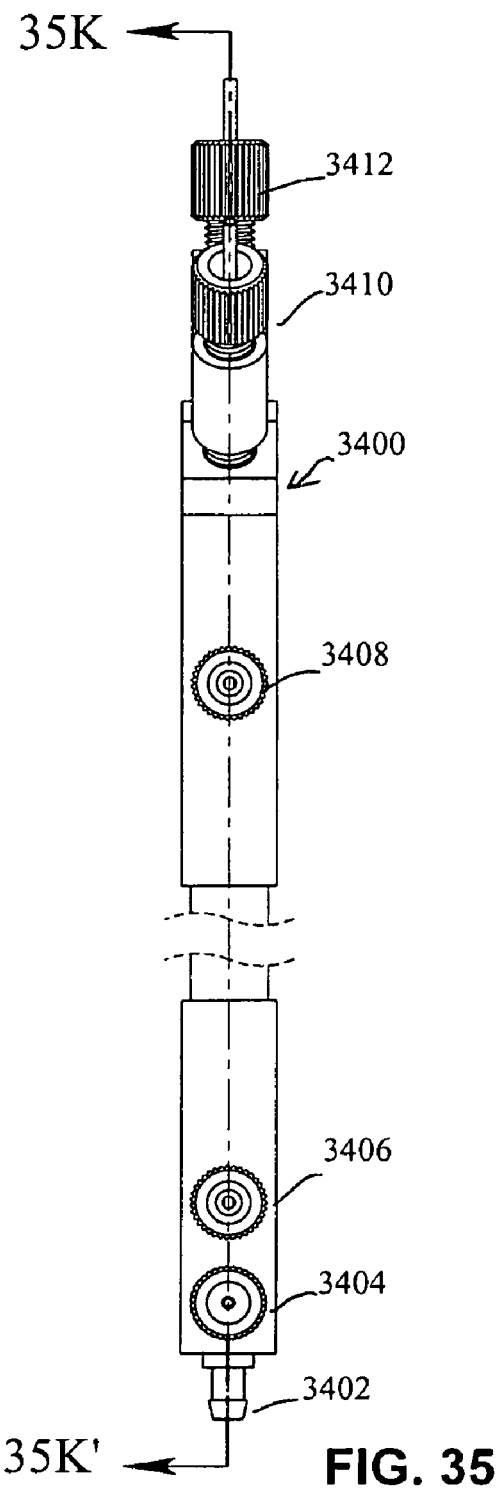
Figure 36:
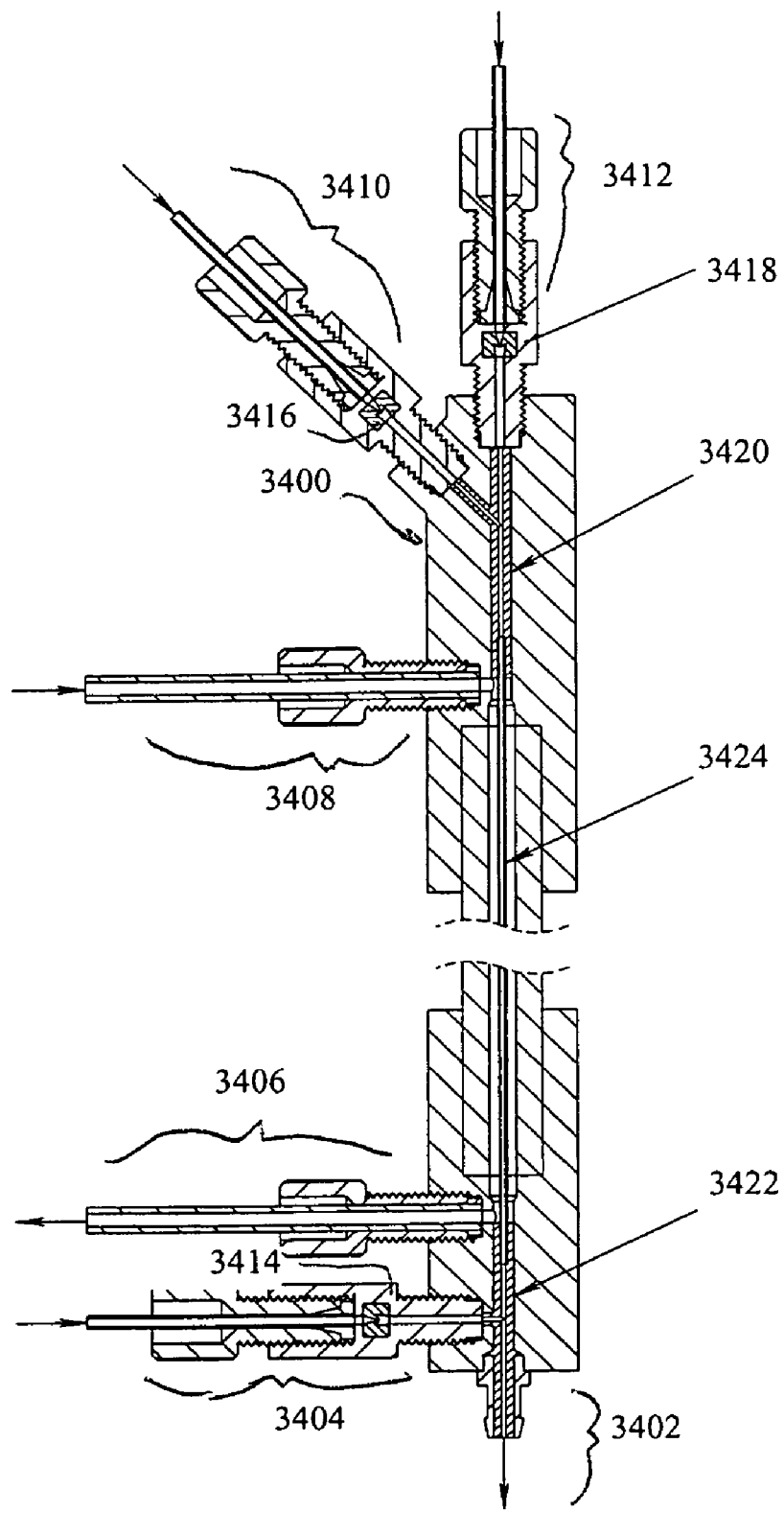

FIGS. 34, 35, and 36 show an embodiment according to concentrator cell 3400, which is designed for long, large diameter hollow fiber filters.

FIG. 36 shows each component of concentrator cell 3400 where arrows indicate the direction of flow through each of retentate port 3402, feed port 3404, permeate port 3406, permeate purge port 3408, gas injection port 3410, and extraction foam port 3412. Valves 3414, 3416 and 3418 are one-way check valves. Potting material 3420, 3422 retains hollow fiber filter 3424 and forms fluid channels.

Concentrator cell 3400 operates as follows retentate valve 3402 is opened and a vacuum is applied to the permeate port 3406. The feed solution is injected through the feed port 3404 until it reaches the potting material 3424, then the retentate valve 3402 is closed and the feed pressure is increased. The feed solution forces the gas in the hollow fiber filter 3424 to compress and fill the channel above the fiber while the feed solution is being forced through the hollow fiber filter 3424. When all of the feed solution has been forced through, the permeate purge port 3408 is opened, and the remaining fluid outside the hollow fiber filter 3424 is flushed into the permeate port 3406 while the pressure equalizes across the surface of the hollow fiber filter 3424. Then, gas pressure is applied through the permeate port 3406, and the retentate valve 3402 is opened. A predetermined volume of extraction foam is injected through the extraction foam port 3412 to flush the captured particles off of the inside surface of the hollow fiber filter 3424. Finally, gas is forced through the gas injection port 3410. This forces any remaining foam out of the fiber, producing the desired final volume of concentrated fluid.

Figure 37:
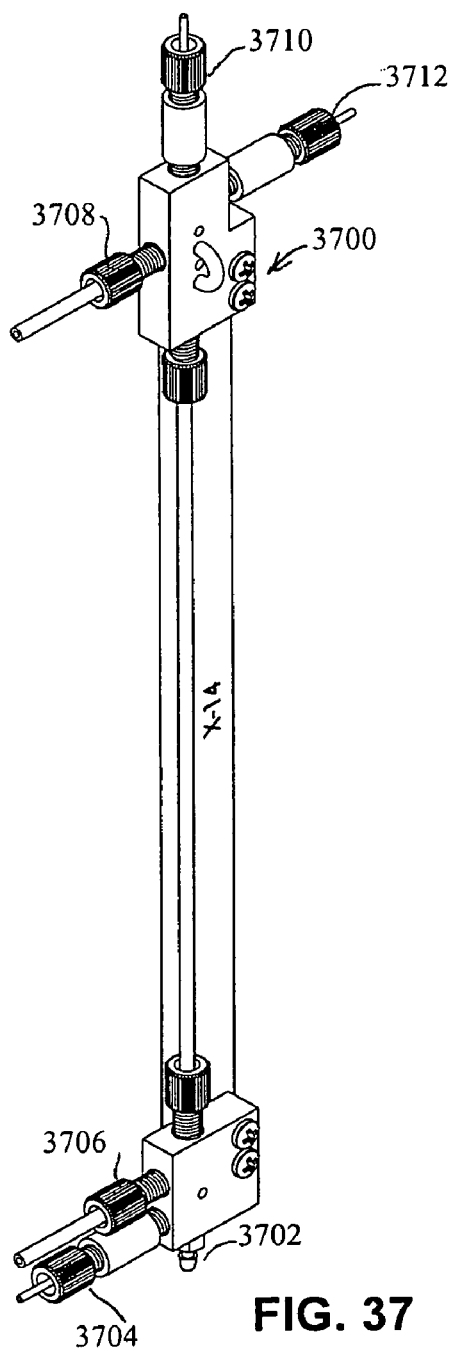
Figure 38:
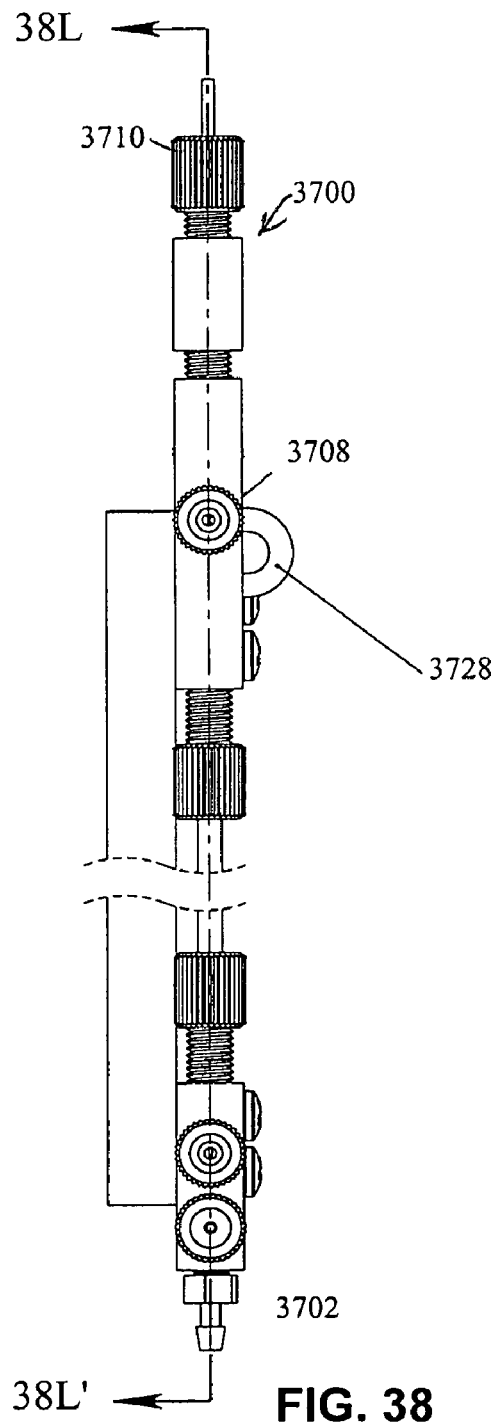
Figure 39:
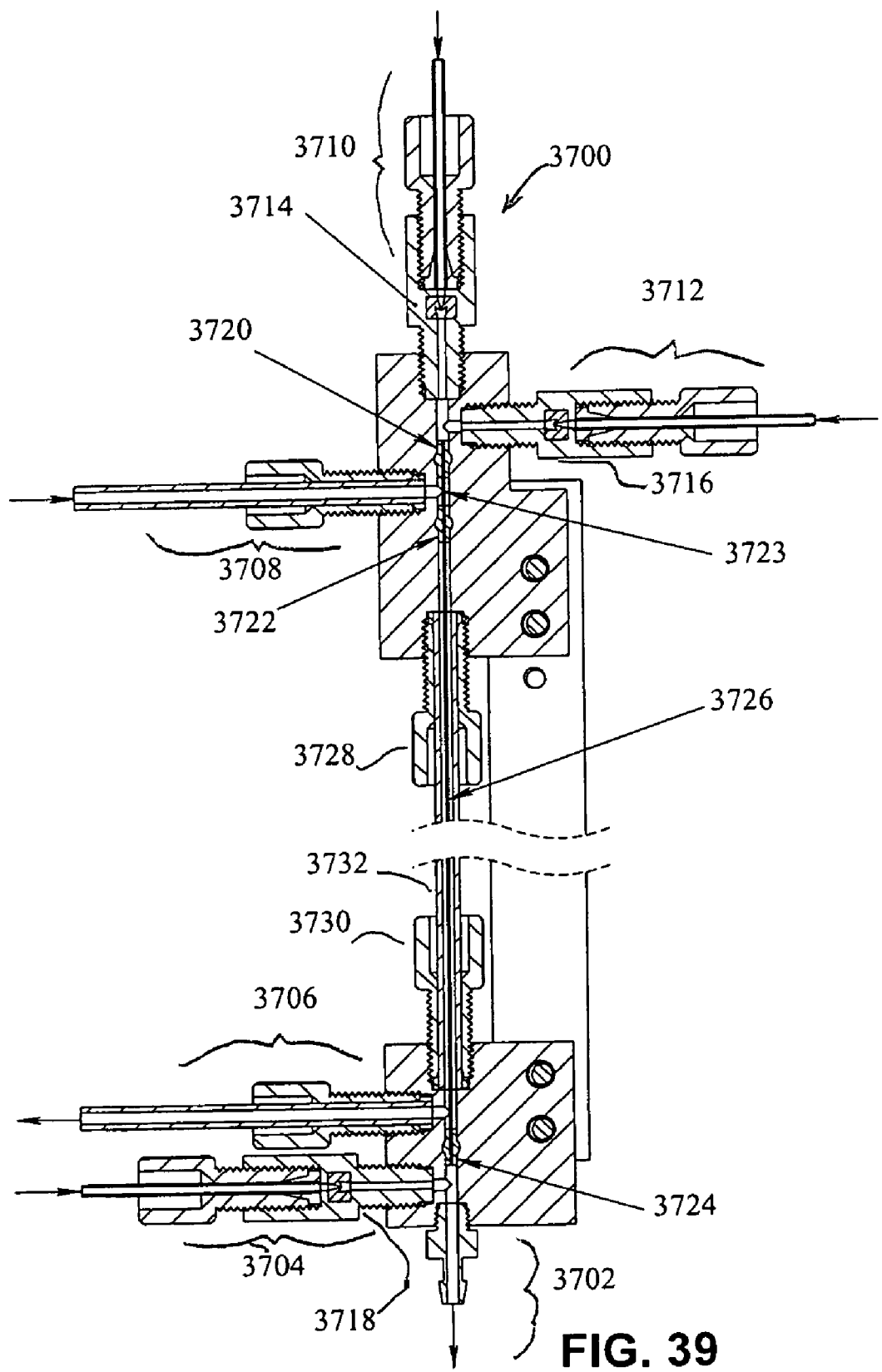

FIGS. 37, 38 and 39 show concentrator cell 3700 which, by way of example. Combines a hydrophobic fiber section with the modular design of concentrator cell 2800. FIG. 39 shows each component of concentrator cell 3700 where arrows indicate the direction of fluid flow in each of retentate port 3702, feed port 3704, permeate port 3706, permeate purge port 3708, extraction foam port 3710, and gas injection port 3712. Valves 3714, 3716, 3718 are one-way check valves. Potting materials 3720, 3722 retain hydrophobic hollow fiber filter while hollow fiber filter 3726 is retained by compression fittings 3728, 3730 and sheath 3732. Tube 3728 connects the permeate channels of the two fibers 3723, 3726.

Concentrator cell operates as follows. Retentate valve 3702 is closed and a vacuum is applied to the permeate port 3706. Feed solution is forced into the feed port 3704. Any gas trapped in the feed side of the fiber is forced out through the hydrophobic fiber 3723. Once the feed solution has all passed through the hydrophilic fiber 3726, the permeate purge 3708 is opened flushing the remaining fluid around the outside of the fiber into the permeate port 3706, and the pressure is equalized across the surface of the fibers. Then, gas pressure is applied through the penneate port 3706, and the retentate valve 3702 is opened. A predetermined volume of extraction foam is injected under pressure through the extraction foam port 3710 to flush the captured particles off of the inside surface of the hollow fiber filter 3726. Finally, gas is forced through the gas injection port 3710, which forces any remaining foam out of the fiber, producing the desired final volume of concentrated fluid.

Figure 40:
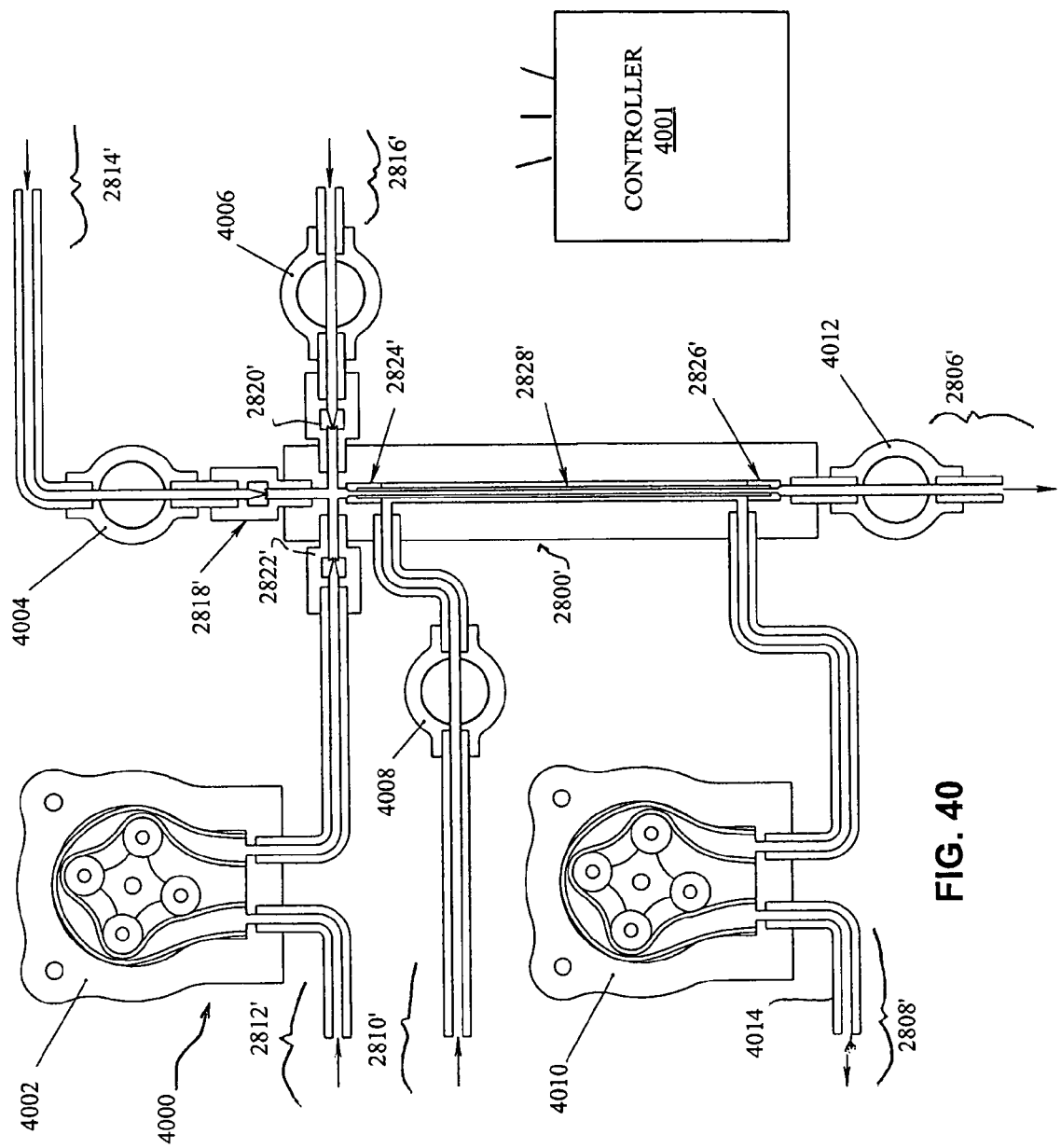

FIG. 40 is a schematic diagram showing an automated system 4000 that may be adapted to incorporate any of the foregoing concentrator cells 100, 400, 700, 1000, 1300, 1600, 1900, 2200, 2500, 2800, 3400, or 3700. In particular as shown, system 4000 incorporates concentrator cell 2800 as described above, together with as well as the extraction foam generator of FIGS. 47-49 below. Carbon dioxide gas as the injection gas. In FIG. 40, like numbering of identical elements is retained with respect to FIG. 30, except a prime "'" is added to designate inclusion of these same elements in system 4000 through communicative fluidic pathways in system 4000. System 4000 additionally includes various elements under automated system control. A system controller is shown generally as controller 4001 and may route control signals to the various elements of system 4000 by circuitry or wireless transmission according to programmable instructions.

Elements of system 4000 under automated controls include a feed pump 4002, an extraction foam valve 4004, gas injection valve 4006, permeate purge valve 4008, permeate pump 4010, and retentate pump 4012.

In the intended environment of use, the feed port 2812' is connected to a reservoir (not shown) which is filled with the feed solution. The permeate purge port 2810' is connected to a filter (not shown) in ambient air. The permeate port 2808' is dumped to another reservoir (not shown) with the opening above the fluid level so air can be pulled back into the line 4014 if the permeate pump 4010 is reversed. The retentate port 2806' is dumped into a sample container (not shown) for analysis. The gas injection port 2816' is connected to a regulated carbon dioxide gas cylinder (not shown). The extraction foam port 2814' is connected to the foam generator (not shown).

System 4000 operates as follows under automated control. The extraction valve 4004, gas injection valve 4006, and permeate purge valve 4008, are all closed while the retentate valve 4012 is opened. The feed solution is poured into the sample reservoir and the feed pump 4002 starts to pump the solution into the cell 2600'. Once the feed solution reaches the bottom of the hollow fiber filter 2828', the retentate valve 4012 is closed, and the permeate pump 4010 starts to pull a vacuum on the permeate side of the hollow fiber filter 2828'. When the feed solution has been completely forced through the hollow fiber filter 2828', the feed pump 4002 reverses slowly to relieve the pressure on the feed side of the hollow fiber filter 2828', and the permeate purge valve 4008 is opened, allowing ambient air to be pulled through the permeate purge port 2810' to flush the permeate fluid out the permeate port 2810'. Then the permeate purge valve 4008 is closed and the permeate pump 4010 is reversed, pressurizing the permeate side of the hollow fiber filter 2828' with air. The retentate valve 4012 is next opened, and then the extraction foam valve 4004 is opened for a timed period allowing a predetermined volume of extraction foam to enter the concentrator cell to flush the captured particles off of the inside surface of the hollow fiber filter 2828'. The gas injection valve 4006 is opened, flushing any remaining foam out the retentate port 2806'.

Figures 41, 41A:
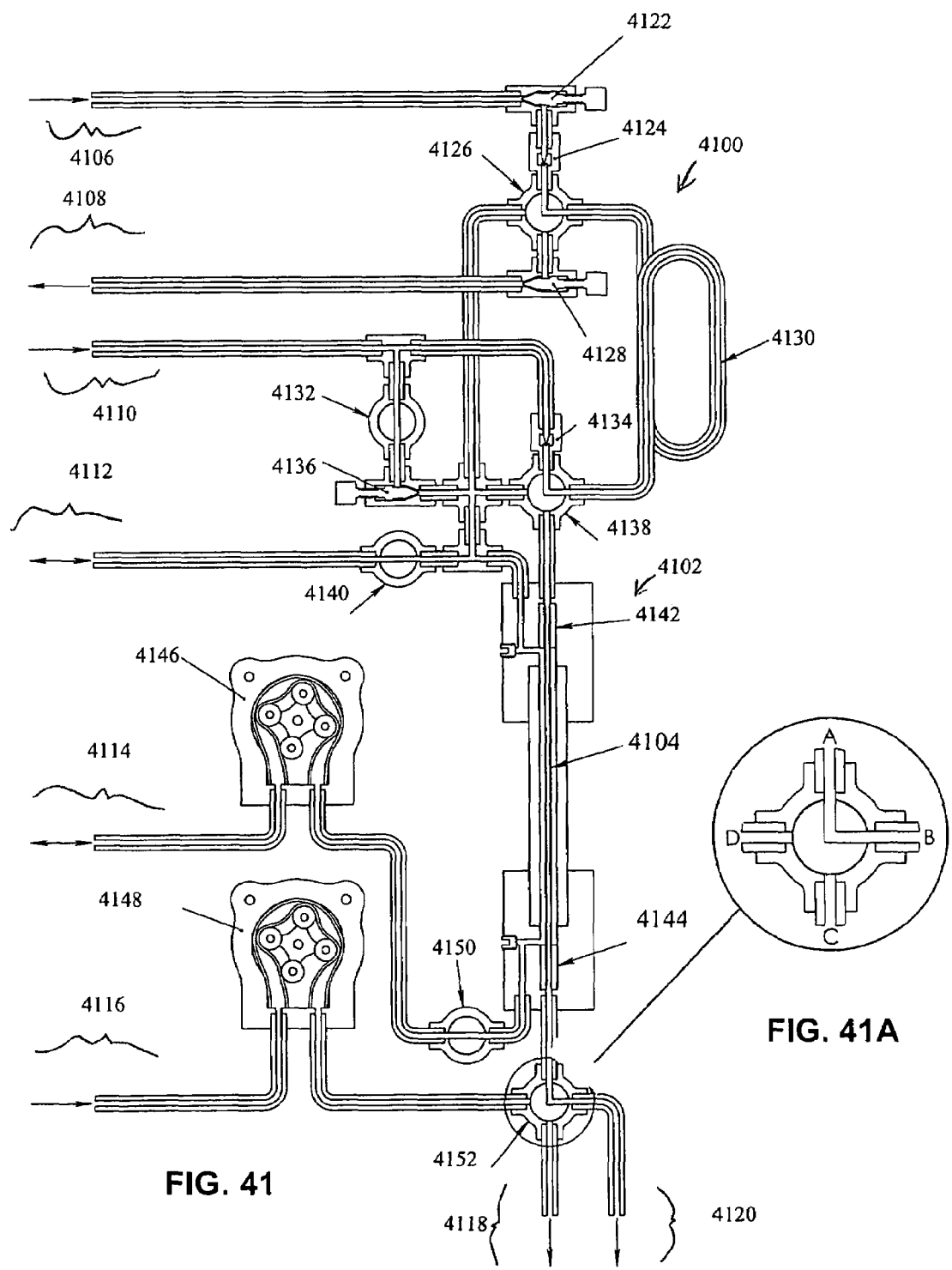

FIG. 41 shows a system 4100 that is designed pressure extraction and high pressure cell storage. When a concentrator cell 4102 is not in use, the system 4100 may pressurize the sample cell 4102 with high pressure gas or high pressure extraction foam to inhibit bacterial growth. System 4100 uses a sample loop, rather than a timed valve, to meter the extraction foam. This allows for higher pressures to be used and more precise control of the final extracted volume. To address the problem of gas on the feed side of a hollow fiber filter 4104, a vacuum is applied to the inside of the fiber to remove any gas before the feed solution is pumped.

System 4100 contains a plurality of components where arrows indicate the direction of fluid movement through elements including high pressure gas port 4106, sample loop overflow (waste) port 4108, extraction foam port 4110, permeate purge port 4112, permeate port 4114, feed port 4116, feed drain port 4118, and retentate port 4120.

Elements of system 4100 under automated control may include gas metering valve 4122 that precedes a high pressure gas one way check valve 4124 downstream from high pressure gas port 4106. A four-position gas valve 4126 may distribute gas through system 4100. There are provided a sample loop metering valve 4128, a sample loop 4130, cell foam storage valve 4132, extraction foam one way check valve 4134, cell foam storage metering valve 4136, the extraction foam valve 4138, and permeate purge valve 4140. Potting materials 4142, 4144 retain the hollow fiber filter 4104. Pumps include the permeate pump 4146 and the feed pump 4148. Numeral 4150 designates the permeate valve, while numeral 4152 designates the retentate valve which is the same type of a four position valve as is valve 4126.

In the intended environment of use, the high pressure gas port 4106 is connected to a regulated gas source (not shown). The sample loop overflow port 4108 is connected to a waste container (not shown). The extraction foam port 4110 is connected to a foam generator (not shown). The penneate purge port 4112 is also connected to the waste container; however it is connected in such a way that when the permeate pump 4146 is pulling vacuum on the cell 4102, ambient air can enter the port 4112. The permeate port 4112 is connected to the permeate reservoir (not shown), however it is connected in such a way that when the permeate pump 4146 is pressurizing the cell 4102, ambient air can enter the port 4112. The feed port 4116 is connected to the feed reservoir (not shown). The feed drain port 4118 is connected to the waste container. The retentate port 4120 is dumped into a sample container (not shown) for analysis.

System 4100 uses HPLC style rotary selection valves. FIG. 41A shows the port labels for the valves, the valve is shown in position AB. When a valve of this type is said to be turned off, it is rotated to the nearest position between ports, preventing any fluid movement. All of the four-way valves in this system 4100 have the same port labels.

The gas metering valve 4122, the sample loop metering valve 4128, and the cell foam storage metering valve 4136 all perform a similar purpose. These valves are used to slow the fluid flow and maintain a high fluid pressure on one side. Shown are adjustable needle valves, however, calibrated orifices could be used in place of needle valves.

The concentration and sample recovery cycle is performed as follows. All valves are initially off. The extraction foam valve 4138 is rotated to position CD, connecting the feed and permeate sides of the hollow fiber filter 4104. The permeate valve 4150 is then opened and the permeate pump 4146 pulls a vacuum on the cell 4102. This removes any gas on the feed side of the hollow fiber filter 4104. Once a vacuum has been created on the feed side of the hollow fiber filter 4104, the extraction foam valve 4138 is turned off and the retentate valve 4152 is rotated to position AD. The feed pump 4148 starts forcing the feed solution through the hollow fiber filter 4104. While the feed solution is being forced through the hollow fiber filter 4104, the gas valve 4126 is rotated to position AB, and the sample loop 4130 is pressurized with high pressure gas. This keeps the extraction foam in liquid form while it is filling the sample loop. Once the sample loop 4130 has been pressurized, the extraction foam valve 4138 rotates to position AB and the gas valve 4126 rotates to position BC. Liquid extraction foam slowly forces out the gas in the sample loop 4130 while the pressure is maintained by the sample loop metering valve 4128. Once the sample loop 4130 has been completely filled with liquid extraction foam, both the gas valve 4126 and the extraction foam valve 4138 are turned off. When all of the feed solution has been forced through the hollow fiber filter 4104, the permeate purge valve 4140 is opened to flush out the remaining permeate from around the outside of the hollow fiber filter 4104, and the feed pump 4148 is reversed until the pressure across the surface of the hollow fiber filter 4104 is equalized. Then, the permeate purge valve 4140 is closed and the permeate pump 4146 is reversed to pressurize the permeate side of the hollow fiber filter 4104. The retentate valve 4152 is now rotated to position AB. Then, the extraction foam valve 4138 is rotated to position BC and the extraction fluid expands into foam as it enters the hollow fiber filter 4104. This scrubs the captured particles off of the inside surface of the fiber and flushes them out the retentate port 4120. Gas valve 4126 is rotated to position AB. Gas flushes the remaining extraction foam out of the sample loop 4130 and through the fiber; producing the desired final volume of concentrated fluid. Finally, all valves are turned off.

When the concentrator cell 4102 is not being used, it may be stored in a high pressure gas environment to inhibit bacterial growth. The high pressure gas storage of the cell is performed as follows: All valves are initially off. The extraction foam valve 4138 is rotated to position CD to connect the feed and permeate sides of the hollow fiber filter 4104. This allows both sides of the hollow fiber filter 4104 to be pressurized evenly, and prevents the fiber from rupturing or collapsing. Now, the gas valve 4126 is rotated to position AD, and gas slowly pressurizes the cell. Once the desired pressure is reached, the gas valve 4126 is turned off. To return the cell to a low pressure state, the gas valve 4126 is rotated to position CD, and the gas is allowed to slowly escape.

When the concentrator cell 4102 will not be used for an extended period of time, it is preferred for it to be stored in a liquid environment. The high pressure foam storage of the cell is performed as follows. All valves are initially off. First, the extraction foam valve 4138 is rotated to position CD to connect the feed and permeate sides of the hollow fiber filter 4104. This allows both sides of the hollow fiber filter 4104 to be pressurized evenly, and prevents the fiber from rupturing or collapsing. Then, the permeate valve 4150 is opened and the permeate pump 4146 pulls a vacuum on the cell 4102 to remove any gas. Once the gas has been removed, the permeate pump 4146 is turned off and the permeate valve 4150 is closed. Now, the cell foam storage valve 4132 is opened and extraction fluid is slowly forced into the cell 4102. The extraction fluid initially expands into foam, however as the pressure increases it collapses back into a liquid. Once the desired pressure is reached, the cell foam storage valve is turned off. To return the cell to a low pressure state, the gas valve 4126 is rotated to position CD and the extraction fluid is allowed to slowly escape. Once the pressure is low enough, the permeate valve 4150 is opened and the permeate pump 4146 pulls a vacuum on the cell 4102 to remove the remaining extraction foam.

Figure 44:
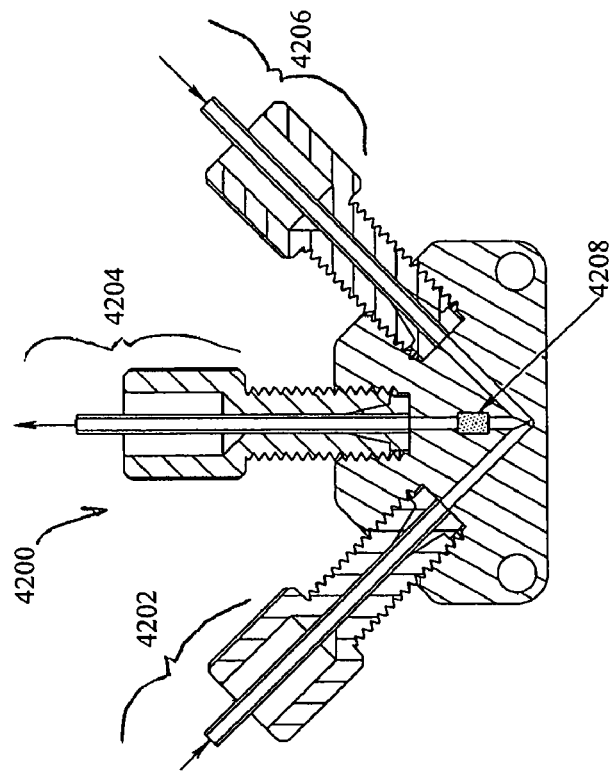
Figure 43:
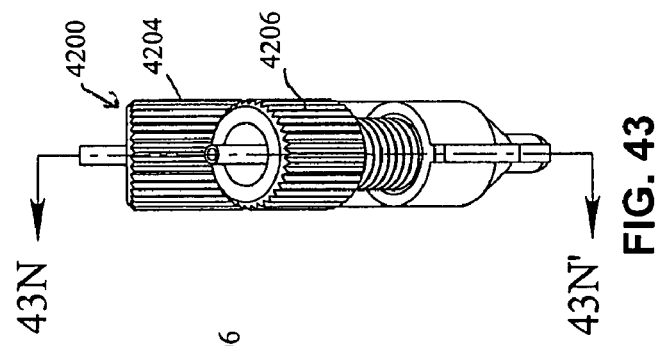
Figure 42:
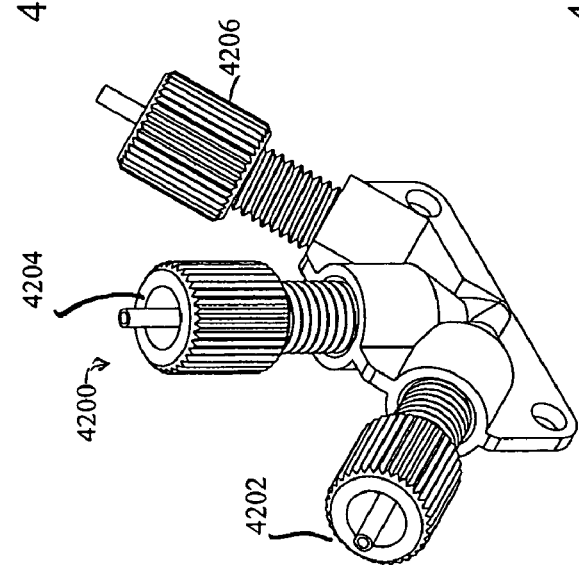

FIGS. 42, 43 and 44 show one embodiment of an extraction foam generator 4200 that may be used to make foam for the extraction purposes discussed above. Foam is created by adding a high pressure gas to a water based solution. In most cases, a surfactant is used in the solution to generate thicker and dryer foam.

FIG. 44 shows each component of the extraction foam generator with arrows indicating the direction of fluid flow in each of gas port 4202, extraction foam port 4204, and is the liquid port 4206. A mixing frit 4208 combines feed from the gas port 4202 and liquid port 4206, ideally to form a solution where the gas is dissolved in the liquid, for foaming discharge at eventual reduced pressure through extraction foam port 4204. Foam is formed in this manner by flashing the gas from the liquid at reduced pressure. Longevity of the foam may be controlled by selecting the type and amount of a particular surfactant.

Extraction foam generator 4200 operates as follows. Gas is injected into the gas port 4202, and a metered amount of liquid extraction solution is injected into the liquid port 4206. The gas and liquid mix in the frit 4208 with the mixture being discharged through extraction foam port 4204. Foam is generated by reducing the pressure on the effluent, or by the mixing action of frit 4208 alone if the pressure at frit 4208 is insufficient to dissolve the gas in the liquid which flows out the extraction foam port 4204.

Figure 46A:
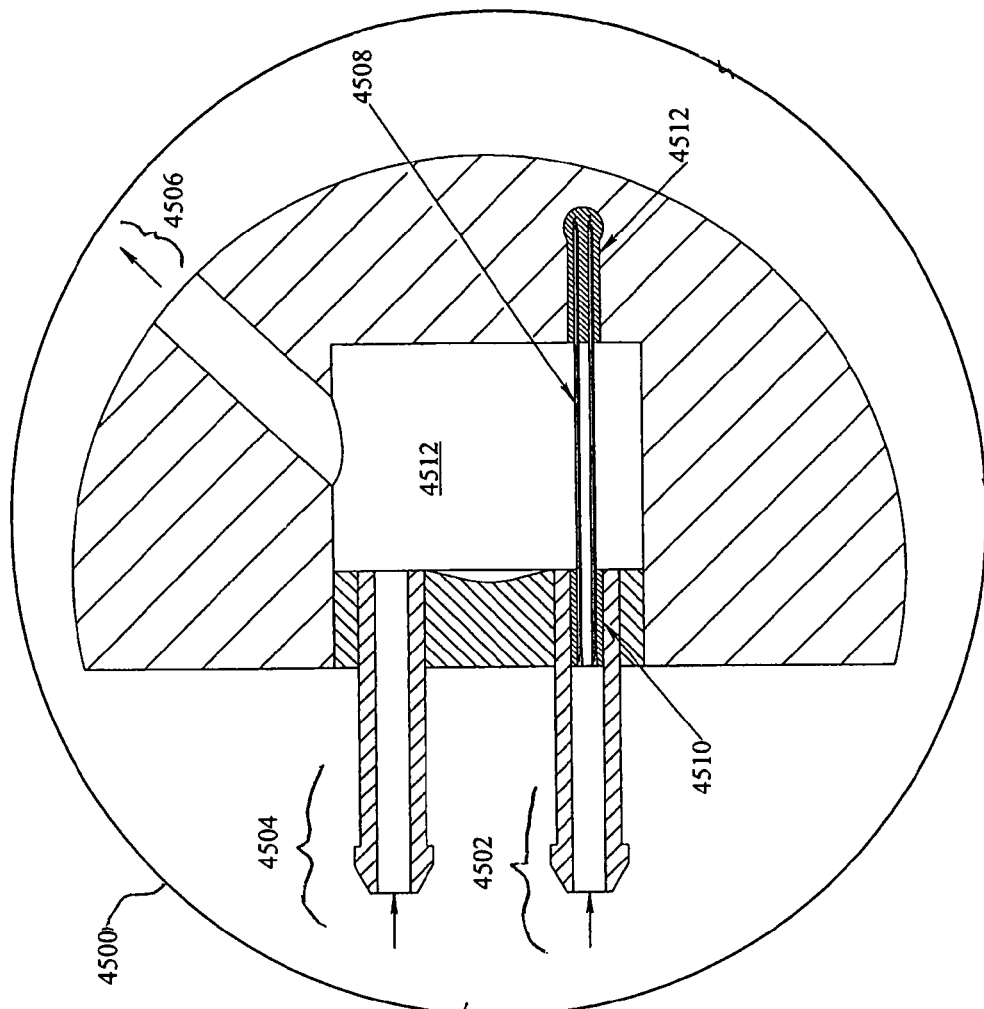
Figure 46:
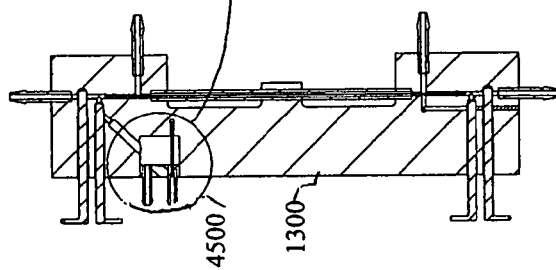
Figure 45:
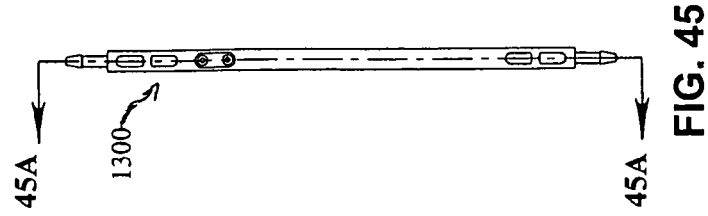

FIGS. 45 and 46 show another embodiment according to extraction foam generator 4500, which is designed to be integrated directly into a concentrator cell (see, e.g., detail 1338 of FIG. 15). FIG. 46 shows the concentrator cell 1300 as previously described. FIG. 46A provides additional detail with respect to the extraction foam generator 4500.

FIG. 46A shows each component of the extraction foam generator 4500 with arrows indicating the direction of fluid flow in each of gas port 4502, liquid port 4504, and foam port 4506. A hollow fiber filter 4508 may be used as a mixing frit, as sealed by potting material 4510, 4512. Foam production is assisted by the action of mixing chamber 4512.

Extraction foam generator 4500 operates as follows. A predetermined volume of liquid extraction solution is injected into the liquid port 4502. High pressure gas is next injected through the gas port 4504 and through the hollow fiber filter 4508. As the gas enters the mixing chamber 4512, the agitation of the liquid generates foam which expands and exists through the foam port 4506.

Figure 49:
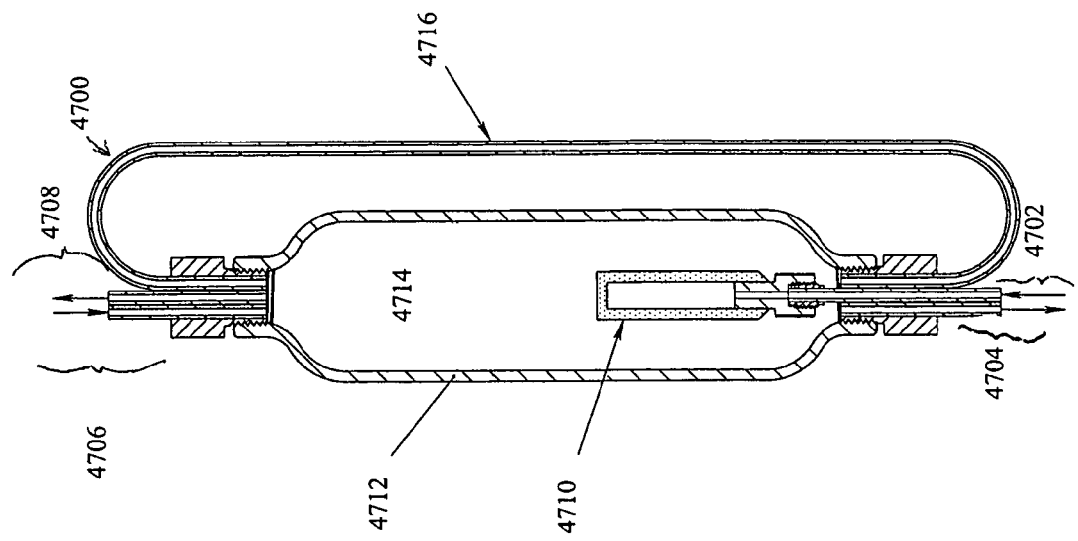
FIG. 49 shows a midsectional view of the extraction foam generator taken along line 48P-48P' of FIG. 48.
Figure 48:
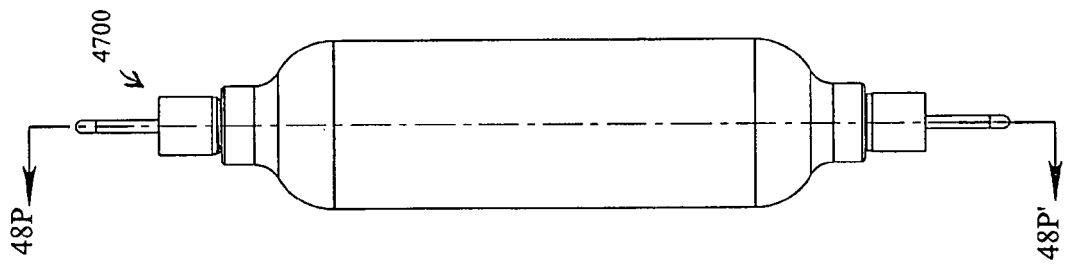
FIG. 48 shows a right side elevational view of the extraction foam generator shown in FIG. 47.
Figure 47:
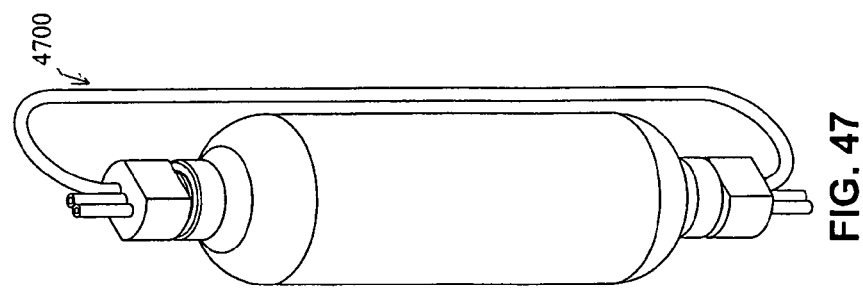
FIG. 47 shows an extraction foam generator according to a third embodiment, as depicted in a three dimensional perspective view.

FIGS. 47, 48 and 49 show yet another embodiment according to extraction foam generator system 4700. System 4700 uses a pressure chamber to force high pressure gas to dissolve into a liquid extraction fluid solution. As long as the extraction fluid is under pressure it remains a liquid, however, if the pressure is reduced it expands into foam.

FIG. 49 shows each component of system 4700 with arrows indicating the direction of fluid flow through gas port 4702, extraction foam port 4704, liquid fill port 4706 and purge port 4708. Foam production is assisted by the action of mixing frit 4710. Wall 4712 defines a chamber 4714. Tube 4716 communicates with pressure chamber 4714 to provide a liquid level indicator and may be translucent for this purpose.

System 4700 operates as follows. The pressure in the chamber 4714 is released through the purge port 4708 and the chamber 4714 is filled with liquid extraction solution through liquid port 4706. Once the pressure chamber is full, the liquid fill port (5) and the purge port (6) are closed off. High pressure gas is injected through the gas port 4702 and through the mixing frit 4710. The gas dissolves into the liquid at the design pressure for operation of chamber 4714, but when the compressed fluid is introduced to a low pressure environment, either before or after discharge through extraction foam port 4704, the gas expands and generates foam.

WORKING EXAMPLES

Performance testing of the device as shown in FIG. 1 above was conducted using carboxylate-coated yellow-green fluorescent polystyrene microspheres (Polysciences, Inc., Warrington, Pa.). Three sizes of microspheres were used; 1 micron, 3 micron, and 4.5 micron diameter. For each test run, 10 mL of a diluted microsphere suspension in water was used as feed. The results of nine 1-micron tests, eight 3-micron tests, and nine 4.5-micron tests were averaged, and the results are summarized graphically in FIG. 5. Note that these tests were performed without surfactant or shear added to the process, and the efficiency ranged from approximately 40% to 65%. Testing of the device was then performed with the addition of 0.01% Triton X-100 surfactant, improving the efficiency of the device to nearly 100%. Efficiency improvement data are shown in Table 1 below.

TABLE 1

Efficiency Improvement using Surfactant
Condition number 16: 3 um carboxylate-coated YG microspheres
Cell efficiency improvement test; 0.01% Triton X-100 Surfactant added

| Sub run # | Feed vol (mL) | Ret. Vol (mL) | Concentration factor | Volume reduction % | Cell efficiency % |
|---|---|---|---|---|---|
| 1 | 10.0 | 0.235 | 43.5 | 97.7 | 102 |
| 2 | 10.0 | 0.157 | 50.6 | 98.4 | 79 |
| 3 | 10.0 | 0.255 | 39.3 | 97.4 | 101 |

TABLE 1-continued

Efficiency Improvement using Surfactant
Condition number 16: 3 um carboxylate-coated YG microspheres
Cell efficiency improvement test; 0.01% Triton X-100 Surfactant added

| Sub run # | Feed vol (mL) | Ret. Vol (mL) | Concentration factor | Volume reduction % | Cell efficiency % |
|---|---|---|---|---|---|
| 4 | 10.0 | 0.274 | 39.3 | 97.3 | 108 |
| 5 | 10.0 | 0.189 | 52.5 | 98.1 | 99 |
| 6 | 10.0 | 0.254 | 42.1 | 97.5 | 107 |
| 7 | 10.0 | 0.228 | 48.1 | 97.7 | 109 |
| Condition average: | | | 45.1 | | 100.7 |

Biological Particle Concentration Data

The device shown in FIG. 4 was used to process a set of nine 10 mL samples of *Bacillus subtilis* spores suspended in phosphate buffered saline solution containing 0.01% Triton X-100 surfactant. The average concentration factor was 65%× with an average efficiency of 59%. These data are summarized in Table 2.

TABLE 2

Biological Particle Enrichment and Throughput Efficiency

| Sample number | Enrichment factor | Efficiency | final concentrate vol. (mL) |
|---|---|---|---|
| 1 | 70 | 64% | 0.093 |
| 2 | 99 | 92% | 0.1362 |
| 3 | 68 | 63% | 0.2276 |
| 4 | 58 | 53% | 0.1236 |
| 5 | 46 | 42% | 0.1053 |
| 6 | 63 | 58% | 0.1544 |
| 7 | 41 | 38% | 0.129 |
| 8 | 63 | 58% | 0.1401 |
| 9 | 70 | 65% | 0.1295 |
| Average | 65 | 59% | 0.1387 |

Foam Concentration Data

One test was conducted using 4.5 micron diameter carboxylate coated yellow-green fluorescent polystyrene microspheres, which were concentrated using the device of FIG. 1 combined with the foam generating attachment described in FIG. 42. The 10 mL samples were reduced to a final volume of 13 microliters with a concentration factor of 688× and the volume reduction was 99.87% with an efficiency of 89.2%.

TABLE 3

Foam extraction efficiency at various foam concentrations

| Test no. | Feed (FIU) | Feed vol (mL) | Sample vial tare (g) | Sample + vial (g) | Dilution factor | Sample average (FIU) | Sample Vol (mL) | Concentration factor | Volume reduction (%) | Concentration efficiency (%) |
|---|---|---|---|---|---|---|---|---|---|---|
| A | 1066 | 10.0 | 1.972 | 2.001 | 0.010 | 2384 | 0.030 | 229 | 99.705 | 67.6 |
| B | 1066 | 10.0 | 1.979 | 2.000 | 0.007 | 2362 | 0.021 | 317 | 99.789 | 66.8 |
| C | 1066 | 10.0 | 1.966 | 1.975 | 0.003 | 3056 | 0.009 | 991 | 99.913 | 86.0 |
| D | 1066 | 10.0 | 1.977 | 1.982 | 0.002 | 2639 | 0.005 | 1518 | 99.951 | 74.2 |

The dilution factor is calculated as the sample weight in grams/3 grams added fluid + sample weight in grams, as the concentrated sample must be diluted for analysis.

A set of test runs was conducted using bacterial endospores (*Bacillus atrophaeus*, ATCC 6633, MedTox, Inc.). Which were concentrated using the device of FIG. 7, combined with the foam generating attachment described in FIG. 42. The 10 mL samples were reduced to an average final volume of 271 microliters with a concentration factor of 63× with an efficiency of 53%. The consistency of performance in the extraction volumes was improved by partially automating the extraction cell. An Omron electronic timer was used in conjunction with a solenoid valve and trigger button to control foam injection times to within 0.001 second. For these experiments, the timer was set to 0.020 seconds for the first 3 extractions, and to 1.020 seconds for the final rinse (extraction 4). The solenoid valve was modified to reduce the interior dead volume by potting a length of Teflon tubing into it for attachment to the concentration cell. The fiber filter used was 0.5 mm ID ME with 0.2 micron pore size, approximately 10 cm long.

TABLE 4

Bacterial spore concentration assessments

| Condition number 34 | Ret. Vol (mL) | Concentration factor | Volume reduction (%) | Efficiency (%) | Total conc. factor | Total extract vol (mL) | Total efficiency (%) |
|---|---|---|---|---|---|---|---|
| Run A - Feed | 0.094 | | | | | | |
| Run A - extract 1 | 0.083 | 25.62 | 99.175 | 21.143 | | | |
| Run A - extract 2 | 0.089 | 2.21 | 99.111 | 1.970 | | | |
| Run A - extract 3 | 0.093 | 1.51 | 99.072 | 1.400 | 29.3 | 0.264 | 24.5 |
| Run A - Rinse | 0.472 | 0.64 | 95.278 | 3.042 | | | |
| Run B - Feed | 0.102 | | | | | | |
| Run B - extract 1 | 0.083 | 3.49 | 99.169 | 2.899 | | | |
| Run B - extract 2 | 0.104 | 0.89 | 98.963 | 0.921 | | | |
| Run B - extract 3 | 0.095 | 0.68 | 99.050 | 0.645 | 5.1 | 0.282 | 4.46 |
| Run C - Rinse | 0.391 | 0.37 | 96.094 | 1.439 | | | |
| Run C - Feed | 0.218 | | | | | | |
| Run C - extract 1 | 0.086 | 37.13 | 99.139 | 31.971 | | | |
| Run C - extract 2 | 0.104 | 2.24 | 98.965 | 2.316 | | | |
| Run C - extract 3 | 0.100 | 1.82 | 99.001 | 1.817 | 41.2 | 0.290 | 36.1 |
| Run C - Rinse | 0.409 | 0.81 | 95.910 | 3.308 | | | |
| Run D - Feed | 0.101 | | | | | | |
| Run D - extract 1 | 0.079 | 45.00 | 99.205 | 35.774 | | | |
| Run D - extract 2 | 0.102 | 2.87 | 98.981 | 2.927 | | | |
| Run D - extract 3 | 0.096 | 1.75 | 99.043 | 1.670 | 49.6 | 0.277 | 40.4 |
| Run D - Rinse | 0.479 | 0.63 | 95.215 | 3.013 | | | |
| Run E - Feed | 0.100 | | 98.997 | | | | |
| Run E - extract 1 | 0.083 | 129.84 | 99.172 | 107.504 | | | |
| Run E - extract 2 | 0.101 | 8.77 | 98.993 | 8.830 | | | |
| Run E - extract 3 | 0.097 | 1.96 | 99.032 | 1.900 | 140.6 | 0.280 | 118 |
| Run E - Rinse | 0.384 | 0.62 | 96.158 | 2.397 | | | |
| Run F - Feed | 0.099 | | 99.009 | | | | |
| Run F - extract 1 | 0.080 | 108.01 | 99.203 | 86.082 | | | |
| Run F - extract 2 | 0.094 | 4.35 | 99.059 | 4.093 | | | |
| Run F - extract 3 | 0.061 | 2.19 | 99.389 | 1.336 | 114.5 | 0.235 | 91.5 |
| Run F - Rinse | 0.288 | 0.87 | 97.118 | 2.493 | | | |
| | | | | Average: | 63 | 0.271 | 53 |
| | | | | Std. Dev.: | 53 | 0.020 | 43 |

Concentration efficiency of the device shown in FIG. 1 was investigated using carboxylate, a functionally coated biosimulant, on polystyrene microspheres. The efficiencies shown in Table 5, below, are for concentrating 1.5 mL of fluid into 100 μL; this produces concentration factors ranging from 9× to 14×. The processing time was less than 90 seconds.

TABLE 5

Concentration efficiency at various particle sizes

| Particle Size (μm) | Represented Particle | Efficiency |
| --- | --- | --- |
| 4.5 | Agglomerates of bacteria | 95% |
| 1.0 | Single bacteria | 85% |
| 0.05 | Viruses | 75% |
| 0.025 | DNA, Lower limit-viruses | 60% |

It will be appreciated that the foregoing instrumentalities teach by way of example, and not by limitation. Accordingly, those skilled in the art understand that the invention is not limited to what is strictly disclosed, but also pertains to what is understood by those skilled in the art on the basis of the teachings herein. The inventors hereby state their intention to rely, as may be needed, upon the Doctrine of Equivalents to protect the fullness of their rights in what is claimed.

We claim:

1. A method for concentration of biological particulates in a liquid comprising:

flowing a first volume of process feed material that bears particulates entrained in a fluid through a hollow fiber filter to separate an amount of the particulates from the fluid by trapping the amount of particulates on a feed side of the hollow fiber filter;

providing a wash liquid and a water soluble gas under pressure, the wash liquid becoming a foam liquid wash material as the gas is released from under pressure and agitated; and extracting the amount of particulates from the feed side of the hollow fiber filter by flowing the foamed liquid wash material through a fluid path extending from a permeate side of the hollow fiber filter across the hollow fiber filter to the feed side of the hollow fiber filter, the foamed liquid wash material biologically and analytically compatible with the particulates, by opening a valve that is controlled with a timer to dispense reproducible volumes of foam by controlling foam pressure and valve opening time, such that this step of extracting provides a second volume of concentrated particulates in the wash liquid.

2. The method of claim 1 wherein the second volume of the foamed liquid wash material diminishes over time by dissipation of foam until the foamed liquid wash material is no longer foam, but is the wash liquid containing the particulates.

3. The method of claim 1 further comprising adding to the wash liquid at least one material selected from the group consisting of buffers, salts, foaming agents, film formers, polymeric materials, surfactants, particles, microspheres, silica particles, tagging materials, proteins, detergents, and other chemical, fluids or particles.

4. The method of claim 1 wherein at least one of the steps of flowing and extracting is accompanied by applying vibrational energy selected from the group consisting of megasonic energy, ultrasonic energy, and vibration.

5. The method of claim 1 wherein the controllable valve is a rotary valve, and extracting includes using a volumetric sample loop that with actuation of the rotary valve is loaded with the foamed liquid wash material and a highly reproducible amount of foamed liquid wash material is released.

6. The method of claim 1 further comprising applying pressurized gas to the permeate side of the hollow fiber filter to push the foamed liquid wash material through the hollow fiber filter.

7. The method of claim 1 including a step of further comprising using pressurized gas to break up clogs in the fluid path.

8. The method of claim 1 further comprising using pressurized gas to push the foam liquid wash material and captured particulates out when there is a heavy loading of material in the retentate.

9. The method of claim 1 further comprising preparing the process feed material with one or more materials selected from the group consisting of particles, bacteria, viruses, protozoa, DNA, RNA, proteins, toxins, immunomagnetic beads, molecular probes, and molecules.

10. The method of claim 1 wherein of flowing the process feed material entails providing a plurality of concentration cells having hollow fiber filters in series; where the hollow fiber filter surface area decreases with each successive cell.

11. The method of claim 1 wherein flowing the process feed material entails providing a plurality of concentration cells having hollow fiber filters with membranes of different pore sizes deployed in parallel to perform particle size fractionation.

12. The method of claim 1 further comprising placing at least part of the fluid path under high pressure gas to act as a biocide during storage of the hollow fiber filter.

13. The method of claim 1 further comprising injecting air across the hollow fiber filter, which is hydrophilic, by pulling a vacuum on the retentate side of the hollow fiber filter then allowing the fluid to move into the fiber retentate side of the hollow fiber filter.

14. The method of claim 1 further comprising moving air across the hollow fiber filter, which is hydrophilic, by pulling a vacuum on the retentate side and permeate side of the hollow fiber filter at the same time to prevent collapse of the hollow fibers.

15. The method of claim 1 further comprising connecting a reservoir to a retentate portion of the fluid path downstream of the hollow fiber filter such that when fluid is pushed into the hollow fiber filter under pressure a volume of residual air in the hollow fiber filter is compressed into this reservoir and the fluid moves to the hollow fiber filter surface.

16. The method of claim 1 further comprising connecting a hydrophobic membrane to a portion of the fluid path on a retentate side of the hollow fiber filter downstream of the hollow fiber filter to permit passage of a volume of air through the hydrophobic membrane until liquid reaches the hollow fiber filter.

17. The method of claim 1 wherein extracting includes opening a permeate purge valve to remove permeate and facilitate a return to atmospheric pressure on the permeate side of the hollow fiber filter.

18. The method of claim 1 wherein flowing the process feed material includes opening a valve on the retentate side of the hollow fiber filter to facilitate pushing the process feed material into the hollow fiber filter, and to facilitate extracting by sending the foamed liquid wash material into a separate fluid line leading to a downstream processing equipment.

19. The method of claim 18 further comprising adding particulate nanomaterials to capture chemicals from a fluid sample, then concentrating the nanomaterials in the flowing and extracting steps.

20. A device for concentrating biological particulates in a liquid comprising:

a hollow fiber cell containing a hollow fiber filter;

a first reservoir connected to a feed side of the hollow fiber filter, the first reservoir containing a first volume of process feed material that bears particulates entrained in a fluid;

a second reservoir connected to a permeate side of the hollow fiber filter, the second reservoir containing a wash liquid and a water soluble gas under pressure, the wash liquid becoming a foam liquid wash material as the gas is released from under pressure and agitated;

means for flowing the first volume through the hollow fiber filter to separate an amount of the particulates from the fluid by trapping the amount of particulates on the feed side of the hollow fiber filter; and a controllable valve controlling the second reservoir for extracting the amount of particulates from the hollow fiber filter by releasing the foamed liquid wash material to flow through a fluid path extending from the permeate side of the hollow fiber filter across the hollow fiber filter to the feed side of the hollow fiber filter, that is biologically and analytically compatible with the particulates, by opening the controllable valve which is controlled with a timer to dispense reproducible volumes of foam liquid wash material from the second reservoir by controlling foam pressure and valve opening time, such that the extracting provides a second volume of concentrated particulates in the wash liquid.

21. The device of claim 20 wherein the wash liquid includes at least one material selected from the group consisting of buffers, salts, foaming agents, film formers, polymeric materials, surfactants, particles, microspheres, silica particles, tagging materials, proteins, detergents, and other chemical, fluids or particles.

22. The device of claim 20 further comprising means for applying vibrational energy selected from the group consisting of megasonic energy, ultrasonic energy, and vibration to the fluid path.

23. The device of claim 20 wherein the controllable valve is a rotary valve which releases a highly reproducible amount of foamed liquid wash material.

24. The device of claim 20 further comprising a pump for applying pressurized gas to push the foamed liquid wash material through the hollow fiber filter.

25. The device of claim 21 further comprising a pump for applying pressurized gas to break up clogs in the retentate or at another location in the fluid path.

26. The device of claim 20 further comprising a pump for using pressurized gas to push the foam liquid wash material and captured material out when there is a heavy loading of material in the retentate.

27. The device of claim 26 wherein the process feed material includes one or more materials selected from the group consisting of particles, bacteria, viruses, protozoa, DNA, RNA, proteins, toxins, immunomagnetic beads, molecular probes, and molecules.

28. The device of claim 20 wherein the means for flowing the process feed material includes means for placing a plurality of concentration cells having hollow fiber filters in series; where the hollow fiber filter surface area decreases with each successive cell.

29. The device of claim 20 wherein the means for flowing the process feed material entails using a plurality of concentration cells having hollow fiber filters with membranes of different pore sizes deployed in parallel to perform particle size fractionation.

30. The device of claim 20 further comprising a pump for adding a gas to the fluid path under high pressure to act as a biocide during storage of the hollow fiber filter.

31. The device of claim 20 further comprising a pump for moving air across the hollow fiber filter, which is hydrophilic, by pulling a vacuum on the retentate side of the hollow fiber filter then allowing the fluid to move into the fiber retentate side of the hollow fiber filter.

32. The device of claim 20 further comprising a pump for moving air across the hollow fiber filter, which is hydrophilic, by pulling a vacuum on the retentate side and permeate side of the hollow fiber filter at the same time to prevent collapse of the hollow fibers.

33. The device of claim 20 further comprising means for connecting a reservoir to a retentate portion of the fluid path downstream of the hollow fiber filter such that when fluid is pushed into the hollow fiber filter under pressure residual a volume of air in the hollow fiber filter is compressed into this reservoir and the fluid moves to the hollow fiber filter surface.

34. The device of claim 20 further comprising means for connecting a hydrophobic membrane to a portion of the fluid path on a retentate side of the hollow fiber filter downstream of the hollow fiber filter to permit passage of air through the hydrophobic membrane until liquid reaches the hollow fiber filter.

35. The device of claim 20 wherein the means for extracting includes a permeate purge valve that is constructed and arranged both to remove permeate and facilitate a return to atmospheric pressure on the permeate side of the hollow fiber filter.

36. The device of claim 20 wherein the means for flowing the process feed material includes a feed valve on the retentate side of the hollow fiber filter to facilitate pushing the process feed material into the hollow fiber filter, and to facilitate the means for extracting by sending the foamed liquid wash material into a separate fluid line leading to downstream processing equipment.

37. The device of claim 36 including means for adding particulate nanomaterials to capture chemicals from fluid samples, then concentrating the nanomaterials in the flowing and extracting steps.

38. The device of claim 20 wherein the foamed wash liquid material is made using a soluble gas and diminishes over time by dissipation of foam until the foam wash liquid material is no longer foam.

* * * * *